(12) United States Patent
Donovan et al.

(10) Patent No.: US 8,876,833 B2
(45) Date of Patent: Nov. 4, 2014

(54) MULTI-PORT DELIVERY SYSTEM

(75) Inventors: Brian W. Donovan, San Jose, CA (US);
Bryan A. Click, Fremont, CA (US)

(73) Assignee: Kyphon Sarl, Neuchatel (CH)

( * ) Notice: Subject to any disclaimer, the term of this patent is extended or adjusted under 35 U.S.C. 154(b) by 673 days.

(21) Appl. No.: 12/771,812

(22) Filed: Apr. 30, 2010

(65) Prior Publication Data

US 2011/0270181 A1    Nov. 3, 2011

(51) Int. Cl.
*A61M 5/00* (2006.01)
*A61B 17/88* (2006.01)

(52) U.S. Cl.
CPC ......... *A61B 17/8822* (2013.01); *A61B 17/8827* (2013.01)
USPC .................. 606/94; 606/92; 604/27; 604/248

(58) Field of Classification Search
USPC ........ 606/92–94; 604/118, 131, 150, 173, 27, 604/30, 248, 249
See application file for complete search history.

(56) References Cited

U.S. PATENT DOCUMENTS

| | | | | |
|---|---|---|---|---|
| 1,845,479 A | * | 2/1932 | Carpenter | 418/45 |
| 2,469,362 A | * | 5/1949 | Bashark | 137/505 |
| 2,635,620 A | | 2/1951 | Deardorff | |
| 2,811,852 A | * | 11/1957 | Shuck et al. | 73/47 |
| 2,847,678 A | * | 8/1958 | Opuszenski | 623/64 |
| 3,259,077 A | * | 7/1966 | Wiley et al. | 417/505 |
| 3,447,479 A | * | 6/1969 | Rosenberg | 417/271 |
| 3,515,127 A | * | 6/1970 | Reymond | 600/573 |
| 3,817,247 A | * | 6/1974 | Mills | 604/150 |
| 4,103,229 A | * | 7/1978 | Gear | 324/71.1 |
| 4,174,473 A | * | 11/1979 | Brenneman | 200/332.2 |
| 4,328,827 A | | 5/1982 | Enjolras | |
| 4,447,226 A | * | 5/1984 | Mayoral | 604/73 |
| 4,563,175 A | * | 1/1986 | LaFond | 604/155 |
| 4,615,469 A | * | 10/1986 | Kishi et al. | 222/327 |
| 4,730,638 A | | 3/1988 | Hazelton | |
| 4,781,687 A | | 11/1988 | Wall | |
| 4,828,545 A | * | 5/1989 | Epstein et al. | 604/66 |
| 4,979,944 A | * | 12/1990 | Luzsicza | 604/118 |
| 5,014,715 A | * | 5/1991 | Chapolini | 600/485 |
| 5,071,547 A | * | 12/1991 | Cazer et al. | 210/198.2 |
| 5,282,573 A | * | 2/1994 | Reimer | 239/85 |
| 5,305,793 A | | 4/1994 | Cencula | |
| 5,360,320 A | * | 11/1994 | Jameson et al. | 417/4 |

(Continued)

FOREIGN PATENT DOCUMENTS

| | | | | |
|---|---|---|---|---|
| EP | 2022426 A2 | * | 2/2009 | A61B 17/88 |
| JP | 2002349959 | * | 12/2002 | F24H 1/10 |

OTHER PUBLICATIONS

International Search Report, WO2011137062, Nov. 3, 2011.

*Primary Examiner* — Matthew Lawson
*Assistant Examiner* — Zade Coley
(74) *Attorney, Agent, or Firm* — Sorell Lenna & Schmidt LLP

(57) ABSTRACT

A device for delivering material to multiple surgical target locations includes a pressure reservoir selectably coupled to two or more outlets. Coupling the pressure reservoir to a given one of the outlets and pressurizing the pressure reservoir causes flowable material (e.g., bone filler material) to be dispensed from that outlet. A diverter for selectably coupling the pressure reservoir one of the outlets can be configured to trigger a pressure release valve for the pressure reservoir upon switching, thereby preventing unexpected or uncontrolled material delivery from the new outlet in response to sudden high pressure exposure.

20 Claims, 18 Drawing Sheets

(56) References Cited

U.S. PATENT DOCUMENTS

| | | | |
|---|---|---|---|
| 5,466,128 A * | 11/1995 | Brown et al. | 417/254 |
| 5,484,354 A * | 1/1996 | Vukovich et al. | 477/174 |
| 5,567,122 A * | 10/1996 | Schulte | 417/214 |
| 5,643,218 A * | 7/1997 | Lynn et al. | 604/191 |
| 5,670,048 A * | 9/1997 | Davison et al. | 210/634 |
| 5,695,720 A * | 12/1997 | Wade et al. | 422/82 |
| 5,814,015 A * | 9/1998 | Gargano et al. | 604/67 |
| 5,915,313 A * | 6/1999 | Bender et al. | 111/178 |
| 6,264,436 B1 | 7/2001 | Edwards et al. | |
| 6,428,702 B1 * | 8/2002 | Berger et al. | 210/634 |
| 7,025,079 B1 | 4/2006 | Elnar | |
| 7,371,241 B2 | 5/2008 | Evans et al. | |
| 7,967,783 B2 * | 6/2011 | Rebours | 604/121 |
| 8,235,256 B2 * | 8/2012 | Green et al. | 222/389 |
| 2003/0091741 A1 * | 5/2003 | Schmoyer | 427/255.28 |
| 2004/0181206 A1 * | 9/2004 | Chiu et al. | 604/509 |
| 2005/0180806 A1 * | 8/2005 | Green et al. | 401/119 |
| 2005/0209602 A1 | 9/2005 | Bowman et al. | |
| 2007/0039866 A1 * | 2/2007 | Schroeder et al. | 210/265 |
| 2007/0161943 A1 | 7/2007 | Lidgren et al. | |
| 2007/0213660 A1 | 9/2007 | Richards et al. | |
| 2008/0125330 A1 * | 5/2008 | Cady et al. | 506/17 |
| 2008/0249530 A1 | 10/2008 | Truckai et al. | |
| 2011/0301535 A1 * | 12/2011 | Takayama et al. | 604/93.01 |
| 2012/0035471 A1 * | 2/2012 | Lee-Sepsick et al. | 600/432 |
| 2012/0191101 A1 * | 7/2012 | Roth et al. | 606/94 |

* cited by examiner

MULTI-PORT DELIVERY SYSTEM

FIELD OF THE INVENTION

The invention relates to a system and method for performing a surgical procedure, and in particular, to a pressure delivery device that provides multiple output ports in a single instrument.

BACKGROUND OF THE INVENTION

A minimally invasive procedure is a medical procedure that is performed through the skin or an anatomical opening. In contrast to an open procedure for the same purpose, a minimally invasive procedure will generally be less traumatic to the patient and result in a reduced recovery period.

However, there are numerous challenges that minimally invasive procedures present. For example, minimally invasive procedures are typically more time-consuming than their open procedure analogues due to the challenges of working within a constrained operative pathway. In addition, without direct visual feedback into the operative location, accurately selecting, sizing, placing, and/or applying minimally invasive surgical instruments and/or treatment materials/devices can be difficult.

For example, for many individuals in our aging world population, undiagnosed and/or untreatable bone strength losses have weakened these individuals' bones to a point that even normal daily activities pose a significant threat of fracture. In one common scenario, when the bones of the spine are sufficiently weakened, the compressive forces in the spine can cause fracture and/or deformation of the vertebral bodies. For sufficiently weakened bone, even normal daily activities like walking down steps or carrying groceries can cause a collapse of one or more spinal bones. A fracture of the vertebral body in this manner is typically referred to as a vertebral compression fracture. Other commonly occurring fractures resulting from weakened bones can include hip, wrist, knee and ankle fractures, to name a few.

Fractures such as vertebral compression fractures often result in episodes of pain that are chronic and intense. Aside from the pain caused by the fracture itself, the involvement of the spinal column can result in pinched and/or damaged nerves, causing paralysis, loss of function, and intense pain which radiates throughout the patient's body. Even where nerves are not affected, however, the intense pain associated with all types of fractures is debilitating, resulting in a great deal of stress, impaired mobility and other long-term consequences. For example, progressive spinal fractures can, over time, cause serious deformation of the spine ("kyphosis"), giving an individual a hunched-back appearance, and can also result in significantly reduced lung capacity and increased mortality.

Because patients with these problems are typically older, and often suffer from various other significant health complications, many of these individuals are unable to tolerate invasive surgery. Therefore, in an effort to more effectively and directly treat vertebral compression fractures, minimally invasive techniques such as vertebroplasty and, subsequently, kyphoplasty, have been developed. Vertebroplasty involves the injection of a flowable reinforcing material, usually polymethylmethacrylate (PMMA—commonly known as bone cement), into a fractured, weakened, or diseased vertebral body. Shortly after injection, the liquid filling material hardens or polymerizes, desirably supporting the vertebral body internally, alleviating pain and preventing further collapse of the injected vertebral body.

Because the liquid bone cement naturally follows the path of least resistance within bone, and because the small-diameter needles used to deliver bone cement in vertebroplasty procedure require either high delivery pressures and/or less viscous bone cements, ensuring that the bone cement remains within the already compromised vertebral body is a significant concern in vertebroplasty procedures. Kyphoplasty addresses this issue by first creating a cavity within the vertebral body (e.g., with an inflatable balloon) and then filling that cavity with bone filler material. The cavity provides a natural containment region that minimizes the risk of bone filler material escape from the vertebral body. An additional benefit of kyphoplasty is that the creation of the cavity can also restore the original height of the vertebral body, further enhancing the benefit of the procedure.

Typically, kyphoplasty is performed using a bilateral procedure, in which access to the interior of the vertebral body is achieved via pedicular access. Cavities are created in both the left and right halves of the vertebral body interior, and subsequently filled with bone filler material. This bilateral approach can often create a more stable support structure than would be possible using only a unipedicular approach, and can also enhance vertebral body height restoration and maintenance.

However, because conventional cement delivery systems provide only a single delivery output, filling the two cavities can be a cumbersome task. A separate cement delivery system could be used for each cavity, or a single cement delivery system must be moved between the two access cannulas. In either case, the logistics of performing the cement delivery are less than ideal, as the physician performing the procedure is forced to either interact with two separate delivery devices or physically transport a single delivery device between cannulas.

Accordingly, it is desirable to provide surgical tools and techniques that enable user-friendly material delivery during surgical procedures.

SUMMARY OF THE INVENTION

By incorporating a diverter element into a pump with multiple outputs, a material delivery system can service multiple surgical target locations from a single control point.

In various embodiments, a material delivery system can include a pressure reservoir, a pressure source for pressurizing the pressure reservoir, and a diverter for selectably coupling the pressure reservoir to one of multiple outputs. In some embodiments, the pressure reservoir can include a pressure release valve for venting the pressure reservoir to a predetermined baseline pressure (e.g., ambient/atmospheric pressure). The diverter can be configured to trigger (open) the pressure release valve whenever switching between different outputs. Alternatively, the diverter can itself vent the pressure reservoir during switching (e.g., by creating a flow path from the pressure reservoir to the baseline pressure). By automatically venting during the switching process, unintended and/or uncontrolled material delivery can be prevented when the pressure reservoir is initially coupled to the new output. In various embodiments, this vent triggering can occur while one or both of the original and destination outputs are coupled to the pressure reservoir.

In various embodiments, the pressure reservoir can contain a hydraulic fluid that transmits the pressure within the pressure reservoir to a remote material dispensing element (e.g., via hydraulic lines/flexible tubing). The material dispending element then dispenses the actual flowable material (e.g., bone filler material) in response to the pressure transmitted via the hydraulic fluid. In various other embodiments, the pressure reservoir can contain the actual flowable material that is expressed from the pressure reservoir through the selected output.

In various embodiments, a surgical procedure (e.g., kyphoplasty) can be performed using a single material delivery system that includes multiple outputs selectably coupled to a single pressure reservoir. The flowable material can be delivered to each the different surgical target locations individually by manually switching between the different outputs. In various embodiments, switching between different outputs automatically vents the pressure reservoir to a baseline pressure. As a result, sudden high pressure output from the new output can be prevented, thereby minimizing the risk of adverse events during the surgical procedure (e.g., cement extravasation during kyphoplasty or vertebroplasty).

As will be realized by those of skilled in the art, many different embodiments of a multi-output material delivery system, along with systems, kits, and/or methods of using such a material delivery system are possible. Additional uses, advantages, and features of such a material delivery system are set forth in the illustrative embodiments discussed in the detailed description herein and will become more apparent to those skilled in the art upon examination of the following.

DETAILED DESCRIPTION

By incorporating a diverter element into a material delivery system with multiple outputs, the material delivery system can service multiple surgical targets from a single control point.

Figure 1A:
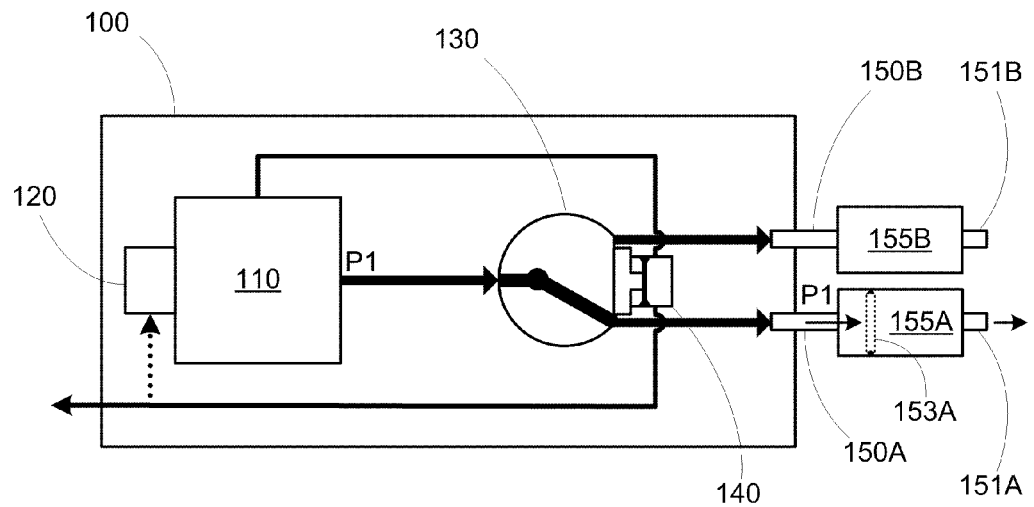
FIGS. 1A-1D show an exemplary schematic diagram of a material delivery system having multiple selectable outputs.

FIG. 1A is a schematic diagram of a material delivery system 100 that includes multiple material dispensing outlets 151. For exemplary purposes, material delivery system 100 is depicted as having two dispensing outlets 151A and 151B, but in various other embodiments, material delivery system 100 can include any number of dispensing outlets 151. Material delivery system 100 further includes a pressure reservoir 110, a pressure source 120, a diverter 130, a pressure release valve 140, pressure outlets 150A and 150B, and material dispensing elements 155A and 155B.

Pressure source 120 can be any system for pressurizing pressure reservoir 110. In one embodiment, pressure source 120 can be a basic hand pump for driving a piston or plunger (e.g., via a squeeze trigger or crank) to pressurize reservoir 110. In various other embodiments, pressure source 120 can be a powered hydraulic pump or precharged pressure vessel coupled to pressure reservoir 110 by a valve. Any number of additional alternatives will be readily apparent.

Diverter 130 selectably couples pressure reservoir 110 to one of pressure outlets 150A and 150B, and therefore to one of material dispensing elements 155A and 155B, respectively. This pressure application causes the recipient material dispensing system 155 to express a flowable material from its associated dispensing outlet 151. Note that "flowable material" as described herein can be any material capable of being dispensed from material delivery system 100, such as PMMA, granulized or pelletized material such as bone morphongenic protein (BMP) or graft material, or even solid materials that can be forced from material dispensing elements 155A and 155B (e.g., wax or phase-change materials). In various embodiments, pressure reservoir 110 can contain the flowable material itself, such that when diverter 130 couples pressure reservoir 110 to, for example, material dispensing element 155A, the flowable material simply flows from pressure reservoir 110 through diverter 130, through material dispensing element 155A, and out of dispensing outlet 151A.

However, in various other embodiments, pressure reservoir 110 can contain a hydraulic fluid (e.g., water, saline solution, or oil, among others) for driving the flowable material from material dispensing elements 155A and 155B. For example, as shown in FIG. 1A, material dispensing element 155A could include a piston 153A that receives hydraulic fluid pressure from pressure reservoir 110, and in response to such pressure forces flowable material out of material dispensing element 155A through dispensing outlet 151A.

In various hydraulic fluid-based embodiments of material delivery system 100, material dispensing elements 155A and 155B could be coupled to pressure outlets 150A and 150B, respectively, by hydraulic lines (e.g., flexible tubing). This would allow dispensing outlets 151A and 151B to be positioned more remotely than would be typically be feasible if the actual flowable material were being forced directly from pressure reservoir 110.

In various other embodiments, material delivery system 100 can also include pressure release valve 140. Pressure release valve 140 is a normally closed valve that, when actuated, vents pressure reservoir 110 to a lower pressure region. Typically, the lower pressure region will be at ambient pressure (e.g., atmospheric pressure), but in various embodiments, the venting can be to a predetermined baseline pressure other than atmospheric pressure. In some embodiments, pressure release valve 140 can vent outside of the pressure system (i.e., an open system) as indicated by the solid arrow, and in other embodiments, pressure release valve 140 can vent back into the pressure system (i.e., a closed system) as indicated by the dotted arrow returning to pressure source 120.

When present, pressure release valve 140 can be triggered by the action of diverter 130. Specifically, switching diverter 130 between outputs can open pressure release valve 140, thereby ensuring that the newly coupled material dispensing element 155 does not receive a sudden high pressure surge. This automatic pressure "reset" prevents unexpected and/or uncontrolled material delivery from the newly selected material dispensing element 155, which can be a critical safety factor during a medical procedure (as described in greater detail below).

For example, in FIG. 1A, diverter 130 is positioned to couple pressure reservoir 110 to material dispensing element 155A. Therefore, as pressure source 120 pressurizes pressure reservoir 110, flowable material is dispensed from dispensing outlet 151A. As described above, this dispensing can be due either to either to hydraulic pressure delivered via a hydraulic fluid in pressure reservoir 110 (e.g., causing piston 153A to force the flowable material from material dispensing element 155A), or to the flowable material being driven from pressure reservoir 110 through diverter 130 and through material dispensing element 155A.

Figure 1B:
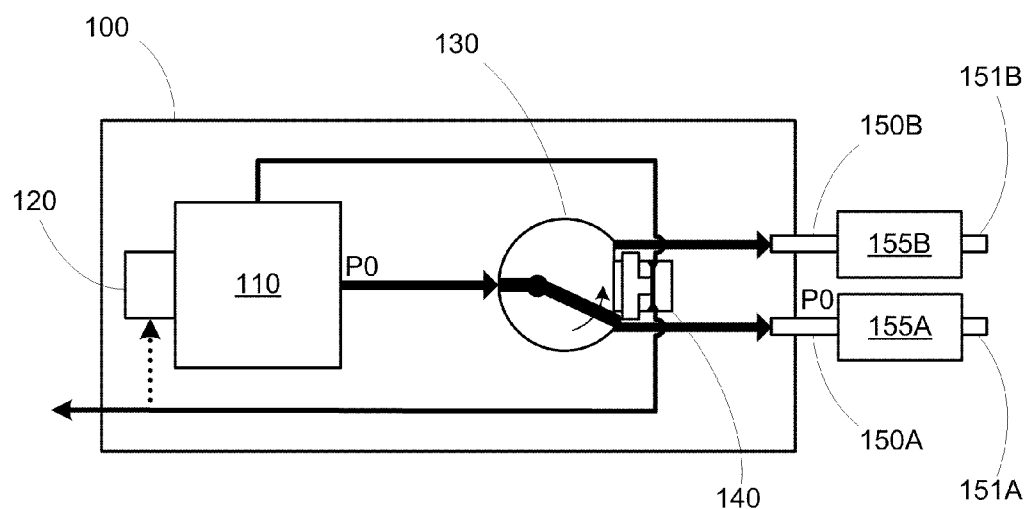

Once a desired amount of flowable material has been expressed from dispensing outlet 151A, diverter 130 can be switched to a new position to couple pressure reservoir 110 to material dispensing element 155B. In one embodiment, as indicated in FIG. 1B, the initiation of this switching operation opens pressure release valve 140, thereby venting pressure reservoir 110. In addition, any residual pressure at material dispensing element 155A can be eliminated by configuring diverter 130 and/or pressure release valve 140 such that pressure release valve 140 opens while diverter 130 is still coupling pressure reservoir 110 to material dispensing element 155A. By doing so, material flow from dispensing outlet 151A can be immediately stopped once switching begins.

Figure 1C:
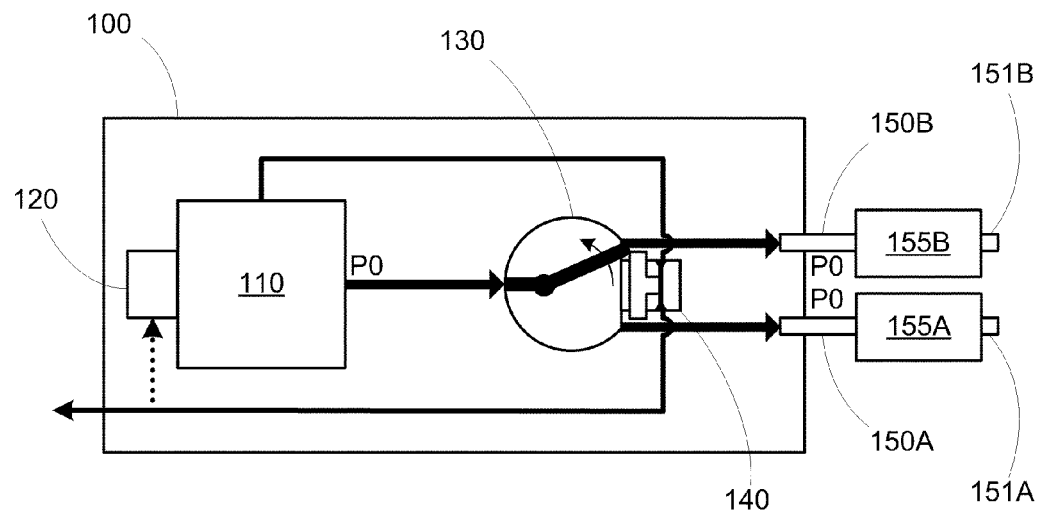

In various embodiments, pressure release valve 140 remains open as diverter 130 couples pressure reservoir 110 to material dispensing element 155B, as shown in FIG. 1C. In doing so, any pressure differential between pressure reservoir 110 and newly connected material dispensing element 155B can be immediately eliminated without creating any unintentional discharge of flowable material from dispensing outlet 151B.

Note that for exemplary purposes diverter 130 is depicted as creating discrete connections between pressure reservoir 110 and material dispensing element 155A and between pressure reservoir 110 and material dispensing element 155B. However, in various other embodiments, diverter 130 can exhibit a mode in which pressure reservoir 110 is simultaneously coupled to both material dispensing elements 155A and 155B. Opening pressure release valve 140 during such a mode would simultaneously equalize pressures at pressure reservoir 110 and material dispensing elements 155A and 155B.

Figure 1D:
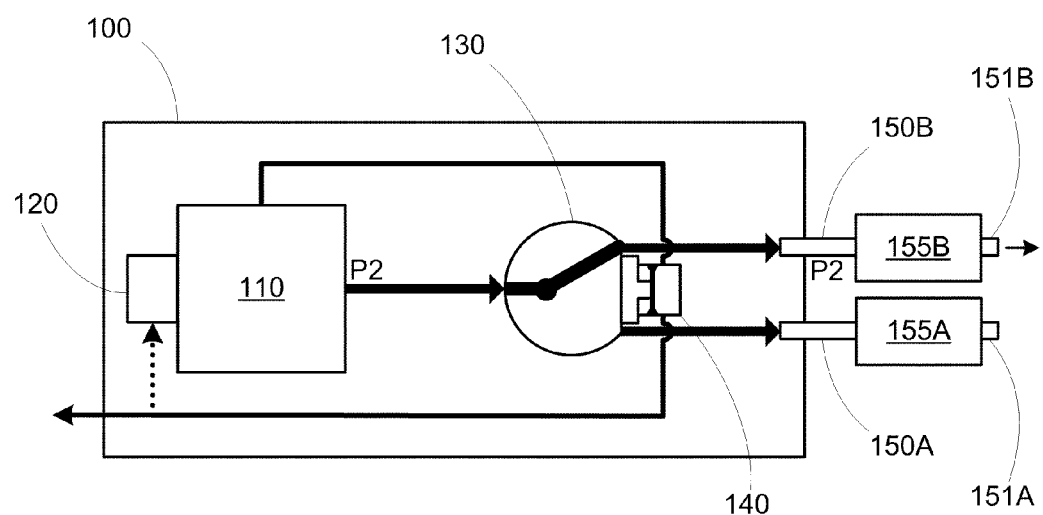

When diverter 130 is fully switched to its new position, pressure release valve 140 is closed, as shown in FIG. 1D. Pressure source 120 can then be used to pressurize pressure reservoir 110 to dispense flowable material from material dispensing element 155B, in a manner substantially similar to that described with respect to material dispensing element 155A in FIG. 1A.

Figure 2A:
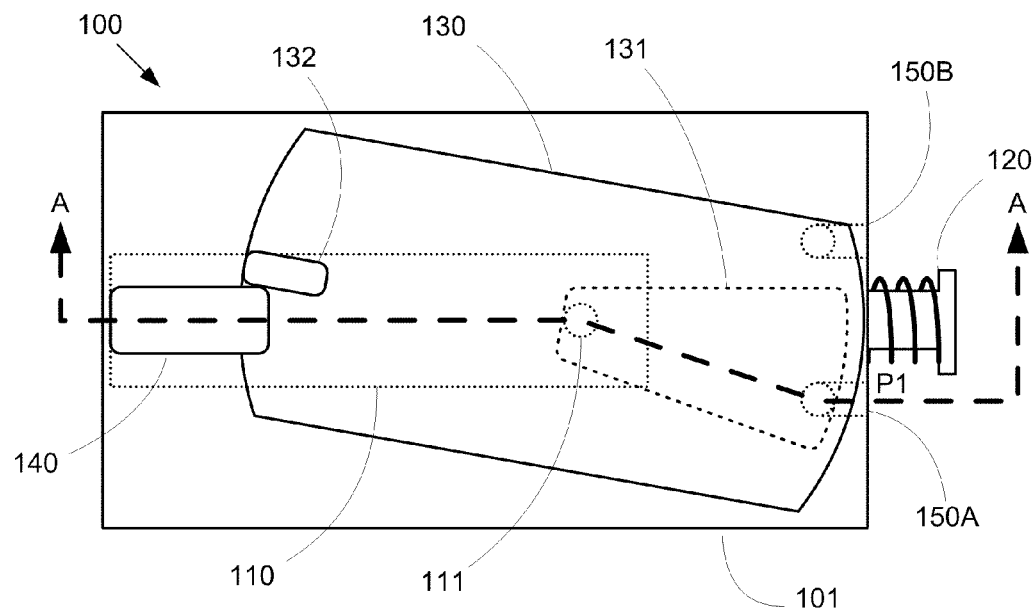
FIGS. 2A-2F show an exemplary implementation of the multi-output material delivery system of FIGS. 1A-1D.
Figure 2B:
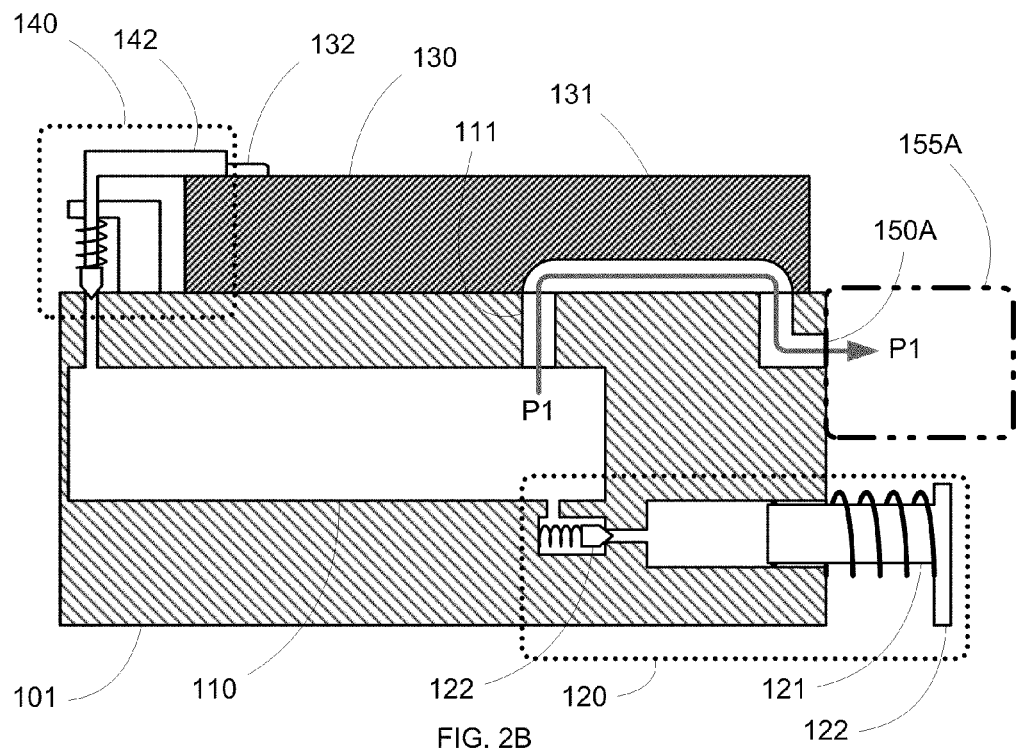

FIG. 2A shows an embodiment of material delivery system 100 (described with respect to FIGS. 1A-1D) in which diverter 130 is a rotational element that defines a flow path 131. In FIG. 2A, flow path 131 is positioned over an outlet 111 of pressure reservoir 110 and an input to pressure outlet 150A. Accordingly, as shown in cross section A-A in FIG. 2B, flow path 131 connects pressure reservoir 110 to pressure outlet 150A, thereby coupling pressure reservoir 110 to material dispensing element 155A (depicted by a phantom outline for simplicity's sake) to dispense flowable material.

Note that while flow path 131 is depicted as a hollowed-out portion of diverter 130 for exemplary purposes, in various other embodiments, flow path 131 can take any configuration or shape. For example, in various embodiments, flow path 131 can be a passageway within diverter 130. Note further that while diverter 130 is depicted and described as a rotational element for exemplary purposes, diverter 130 can exhibit any mode of operation that enables output switching capability. For example, in various embodiments, diverter 130 can be a push-pull element, a rotating ball or cylinder valve, or a movable lever, among others.

For exemplary purposes, pressure generator 120 is depicted as a simple piston 121 that pressurizes pressure reservoir 110 through a one-way check valve 122. Such an embodiment is particularly conducive to pressure generation in a hand-held device. For example, pressure generator 120 can include a trigger 122 that, in response to pressure (e.g., squeezing) by the operator, drives piston 121 inward to pressurize pressure reservoir 110.

Likewise, for exemplary purposes, pressure release valve 140 is depicted as a simple one-way check valve with an actuator 142. Note that in various other embodiments, pressure release valve 140 can incorporate any pressure release mechanism. Raising actuator 142 vents pressure reservoir 110 to ambient pressure (although as described above with respect to FIGS. 1A-1D, in various other embodiments, pressure release valve 140 can be configured to vent to any baseline pressure, either as an open or closed system).

Diverter 130 also includes a triggering feature 132 that is configured to actuate (open) pressure release valve 140 as diverter 130 is rotated. For exemplary purposes, triggering feature 132 is depicted as a raised element on diverter 130 that can slip under actuator 142. Note, however, that in various other embodiments, triggering feature 132 can be any system for actuating pressure release valve 140, including a magnetic switch, a proximity sensor, and/or a mechanical linkage.

Figure 2C:
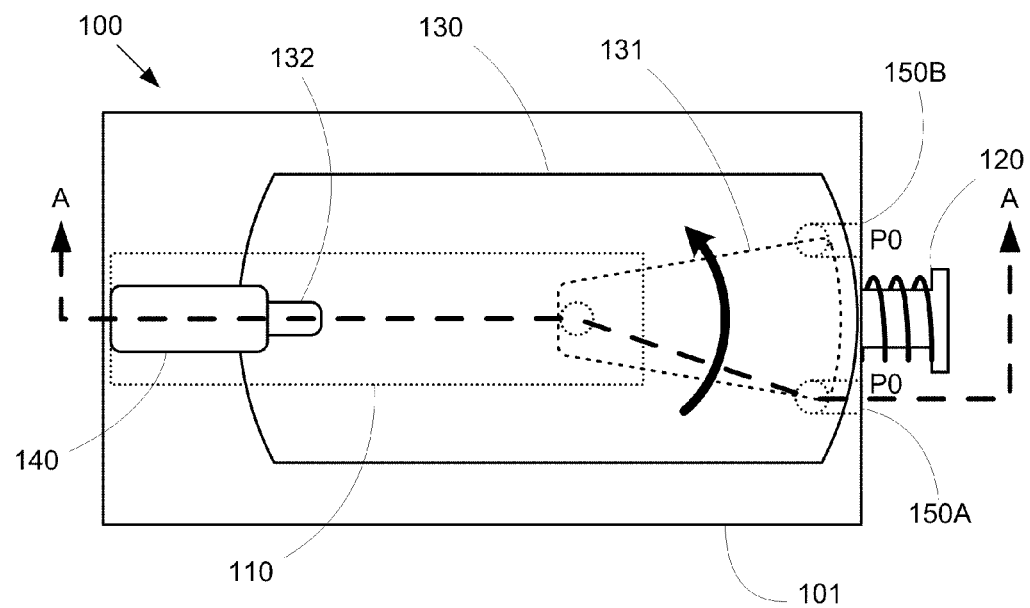
Figure 2D:
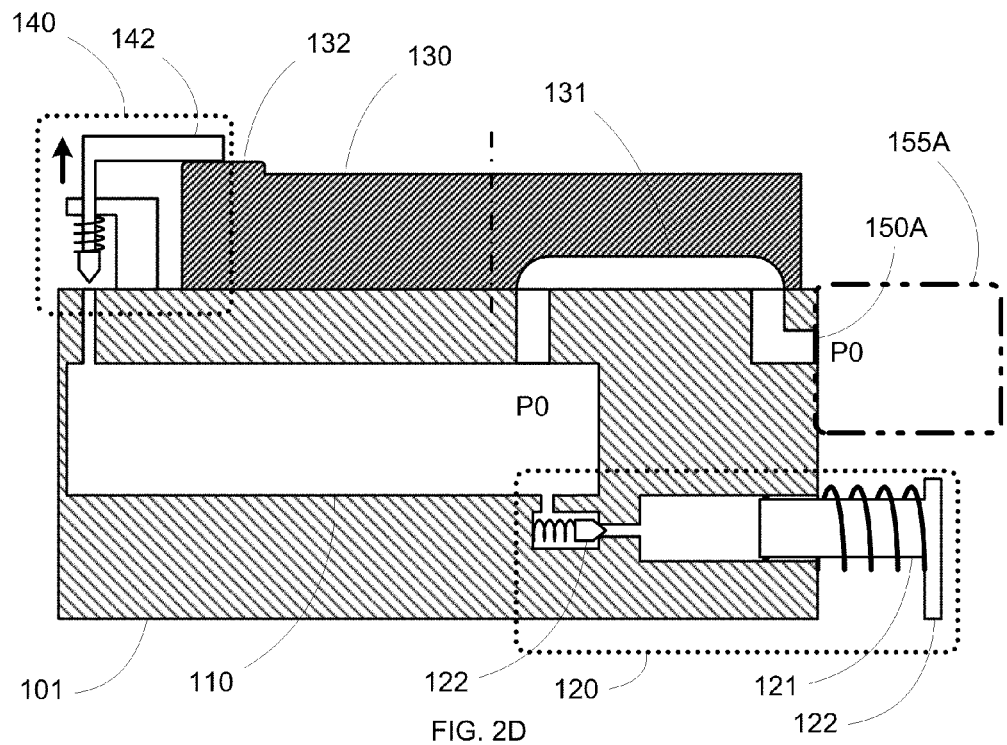

Thus, as diverter 130 is rotated, as shown in FIG. 2C, triggering feature 132 slides under actuator 142, as shown in the cross sectional view of FIG. 2D. This action opens pressure release valve 140, thereby venting pressure reservoir 110 to a baseline pressure P0 (e.g., atmospheric pressure). Because flow path 131 still couples pressure reservoir 110 to pressure outlet 150A, the pressure at material dispensing element 155A is also reduced to baseline pressure P0. As indicated in FIG. 2C, flow path 131 is sized and shaped to also couple pressure reservoir 110 to pressure outlet 150B during the actuation of pressure release valve 140, thereby establishing baseline pressure P0 at pressure outlet 150B (and hence at material dispensing element 155B, which is not shown for clarity).

Figure 2E:
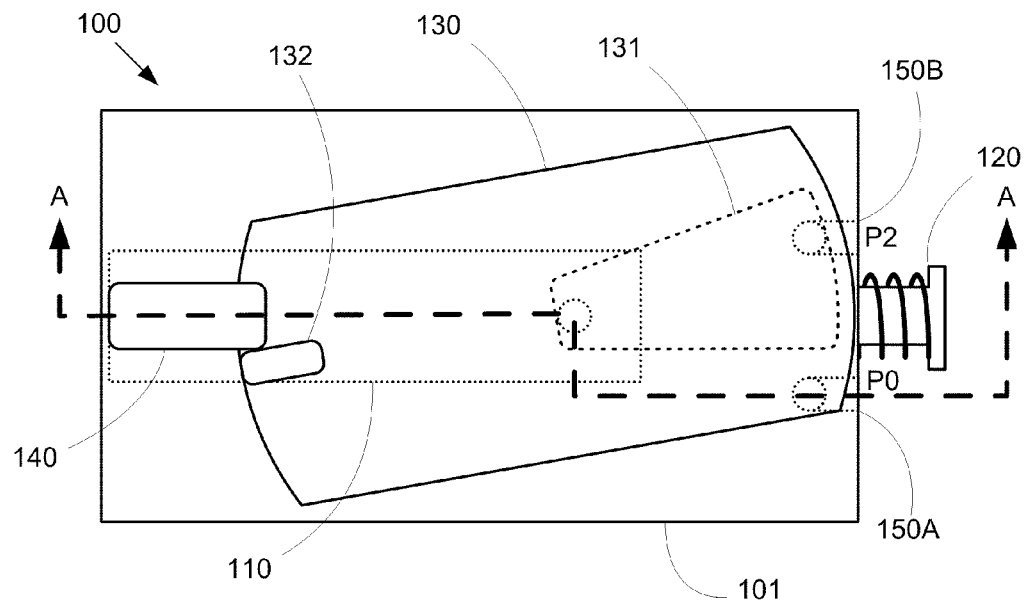
Figure 2F:
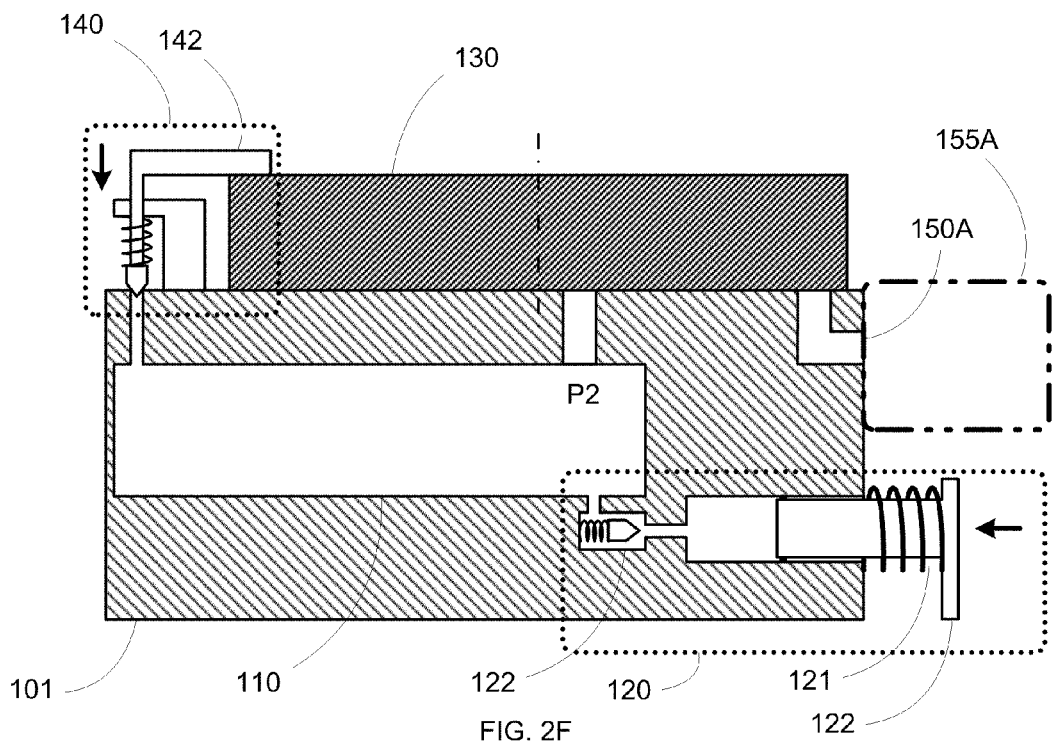

Then, as switching is completed as shown in FIG. 2E, triggering feature 132 is moved out from under actuator 142, thereby closing pressure release valve 140, as shown in cross sectional view A-A in FIG. 2F. Meanwhile, flow path 131 decouples pressure outlet 150A from pressure reservoir 110 (while maintaining the path between pressure reservoir 110 and pressure outlet 150B). Accordingly, as pressure reservoir 110 is pressurized by pressure generator 120 (e.g., by depressing piston 121), the new pressure P2 created within pressure reservoir 110 is transmitted to pressure outlet 150B, while the pressure at pressure outlet 150A remains at the baseline pressure P0.

Note that in various embodiments, diverter 130 can couple pressure reservoir 100 to both pressure outlets 150A and 150B (as shown in FIG. 2C) without triggering pressure release valve 140, (e.g., triggering feature 132 could be absent from diverter 130). In such embodiments, material delivery system 100 could dispense material individually or simultaneously from material dispensing elements 155A and 155B.

Figure 4A:
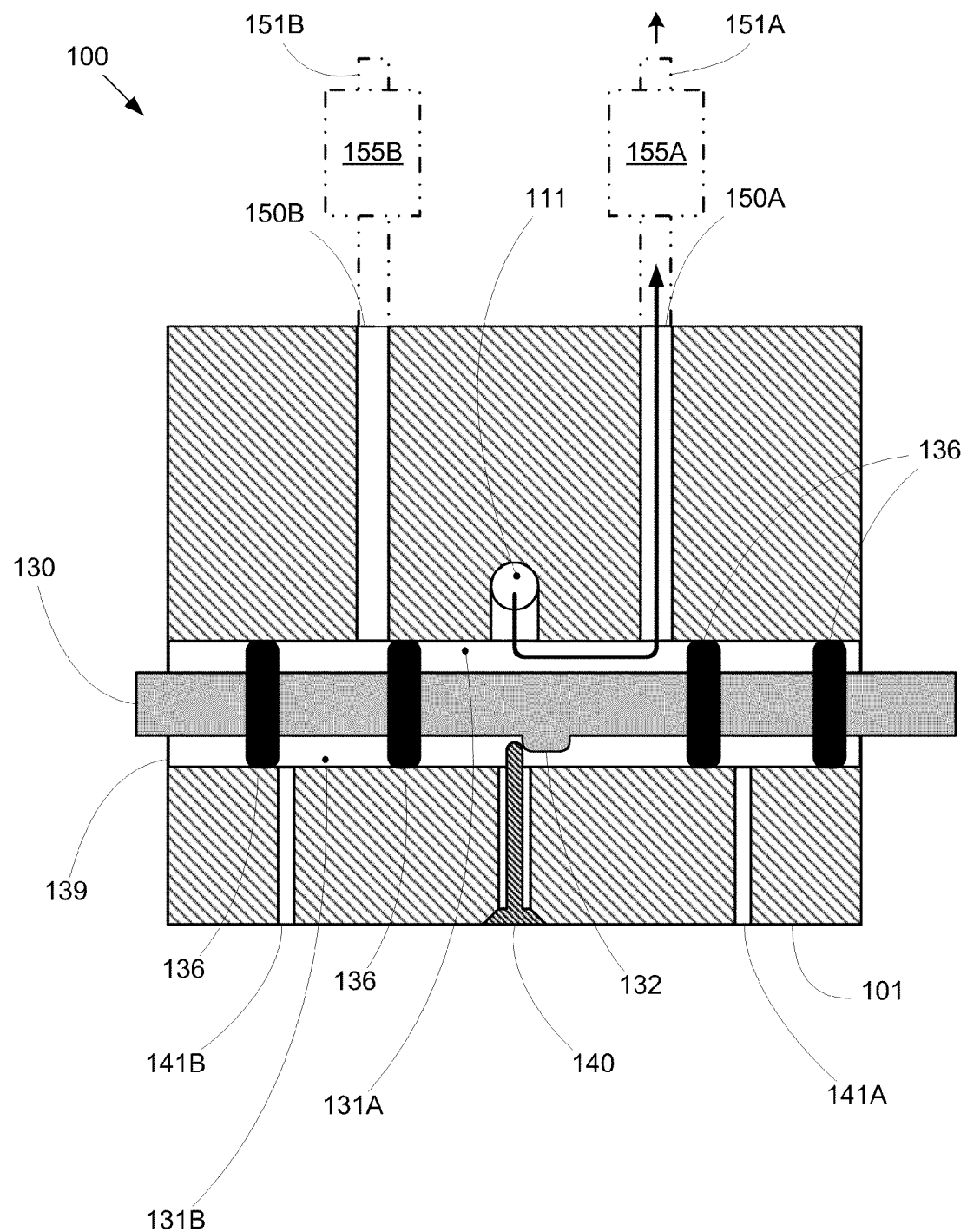
FIGS. 4A-4C show another exemplary implementation of the multi-output material delivery system of FIGS. 1A-1D.

FIG. 4A shows another embodiment of material delivery system 100 (described with respect to FIGS. 1A-1D) in which diverter 130 is a sliding element that defines a primary flow path 131A and a secondary flow path 131B. In particular, diverter 130 is positioned in a passage 139 within housing 101, and includes sealing elements 136 (e.g., o-rings or gaskets) that close passage 139 at various locations. Outlets 150A and 150B, pressure reservoir outlet 111, optional pressure release valve 140, and optional bleed ports 141A and 141B all feed in to passage 139, and are interconnected amongst each other by the particular locations of sealing elements 136.

For example, in FIG. 4A, flow path 131A connects pressure reservoir outlet 111 (the pressure reservoir itself is not shown for simplicity, but can be similar to pressure reservoir 110 described with respect to FIGS. 1A-1D and 2A-2F) to pressure outlet 150A, thereby coupling the pressure reservoir to material dispensing element 155A (depicted by a phantom outline for simplicity's sake) to dispense flowable material, as indicated by the solid arrow. A secondary flow path 131B is created between pressure outlet 150B and bleed port 141B, thereby ensuring that pressure outlet 150B remains at a baseline pressure (e.g., atmospheric pressure) when not actively delivering material from material dispensing element 155B.

Figure 4B:
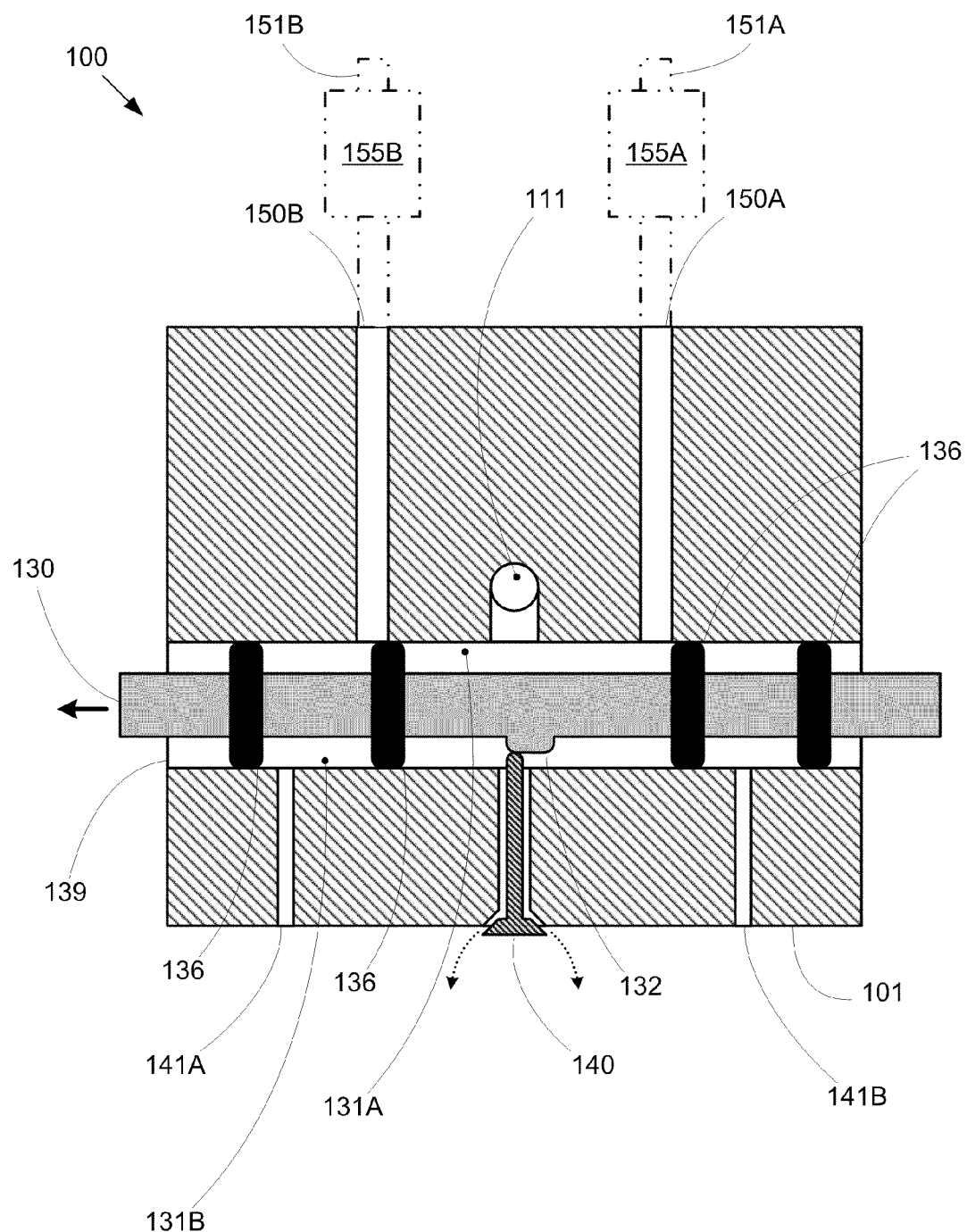

Then, as diverter 130 is moved in the direction indicated by the solid arrow in FIG. 4B, a trigger feature 132 on diverter 130 can actuate optional pressure release valve 140, thereby venting the pressure reservoir (and hence the pressure supplied to material dispensing element 155A), as indicated by the dotted arrows. Note that in various other embodiments, pressure release valve 140 can be eliminated, such that the pressure reservoir is not vented when switching outlets, thereby allowing immediate application of pressure to the newly switched pressure outlet.

Note further that for exemplary purposes, pressure release valve 140 is depicted as a simple one-way check valve. However, as noted above, in various other embodiments, pressure release valve 140 can incorporate any pressure release mechanism. Note further that for exemplary purposes, triggering feature 132 is depicted as a raised element on diverter 130 that can actuate pressure release valve 140. However, in various other embodiments, triggering feature 132 can be any system for actuating pressure release valve 140, including a magnetic switch, a proximity sensor, and/or a mechanical linkage.

Figure 4C:
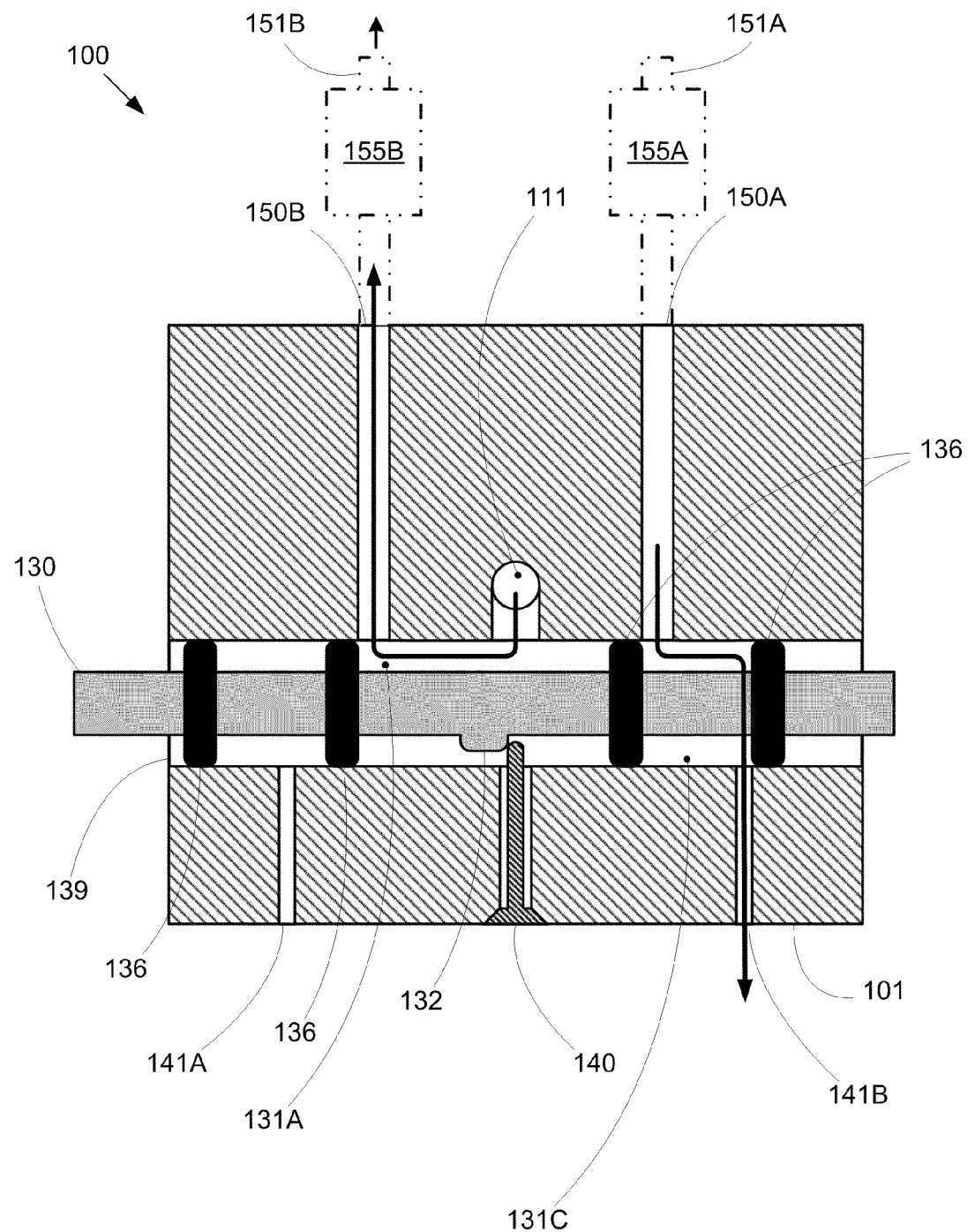

As switching is completed as shown in FIG. 4C, triggering feature 132 allows pressure release valve 140 to close, and the new positions of sealing elements 136 result in flow path 131A connecting pressure reservoir outlet 111 to pressure outlet 150B, thereby coupling the pressure reservoir to material dispensing element 155B to dispense flowable material, as indicated by the solid arrow. A secondary flow path 131C is created between pressure outlet 150A and bleed port 141B, thereby ensuring that pressure outlet 150A remains at a baseline pressure to prevent unintended discharge from material dispensing element 155A.

Figure 5A:
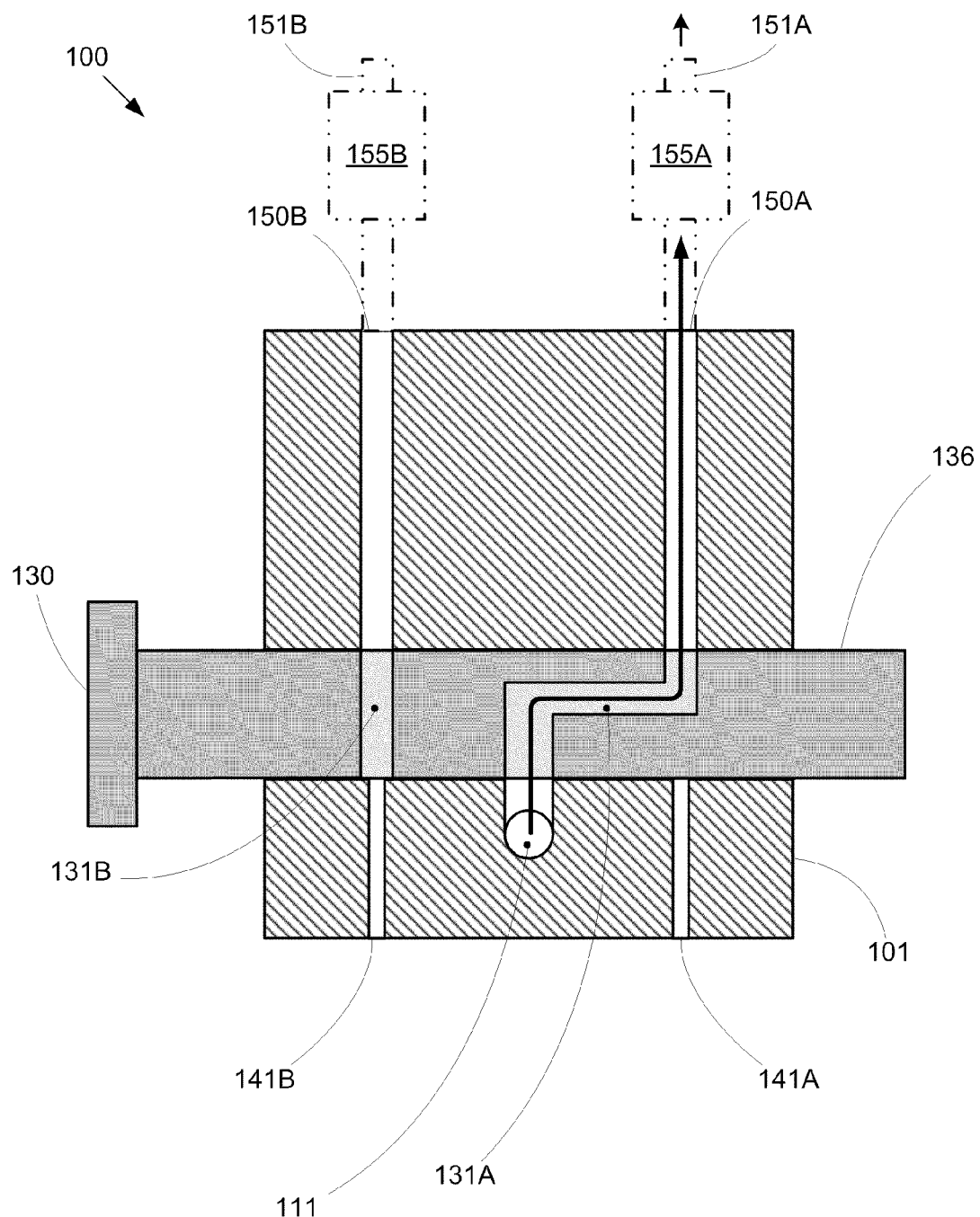
FIGS. 5A-5D show another exemplary implementation of the multi-output material delivery system of FIGS. 1A-1D.

FIG. 5A shows another embodiment of material delivery system 100 (described with respect to FIGS. 1A-1D) in which diverter 130 is an axially-rotatable element that defines a first flow path 131A and a second flow path 131B. Specifically, diverter 130 a cylindrical element positioned within housing 101, with flow paths 131A and 131B formed as channels on the surface of the cylinder. The rotational orientation of diverter 130, and hence, the positions of flow paths 131A and 131B, determines the particular interconnections between outlets 150A and 150B, pressure reservoir outlet 111, and bleed ports 141A and 141B.

For example, in FIG. 5A, flow path 131A connects pressure reservoir outlet 111 (the pressure reservoir itself is not shown for simplicity) to pressure outlet 150A, thereby coupling the pressure reservoir to material dispensing element 155A (depicted by a phantom outline for simplicity's sake) to dispense flowable material, as indicated by the solid arrow. Flow path 131B connects pressure outlet 150B and bleed port 141B, thereby ensuring that pressure outlet 150B remains at a baseline pressure (e.g., atmospheric pressure) when not actively delivering material from material dispensing element 155B.

Figure 5B:
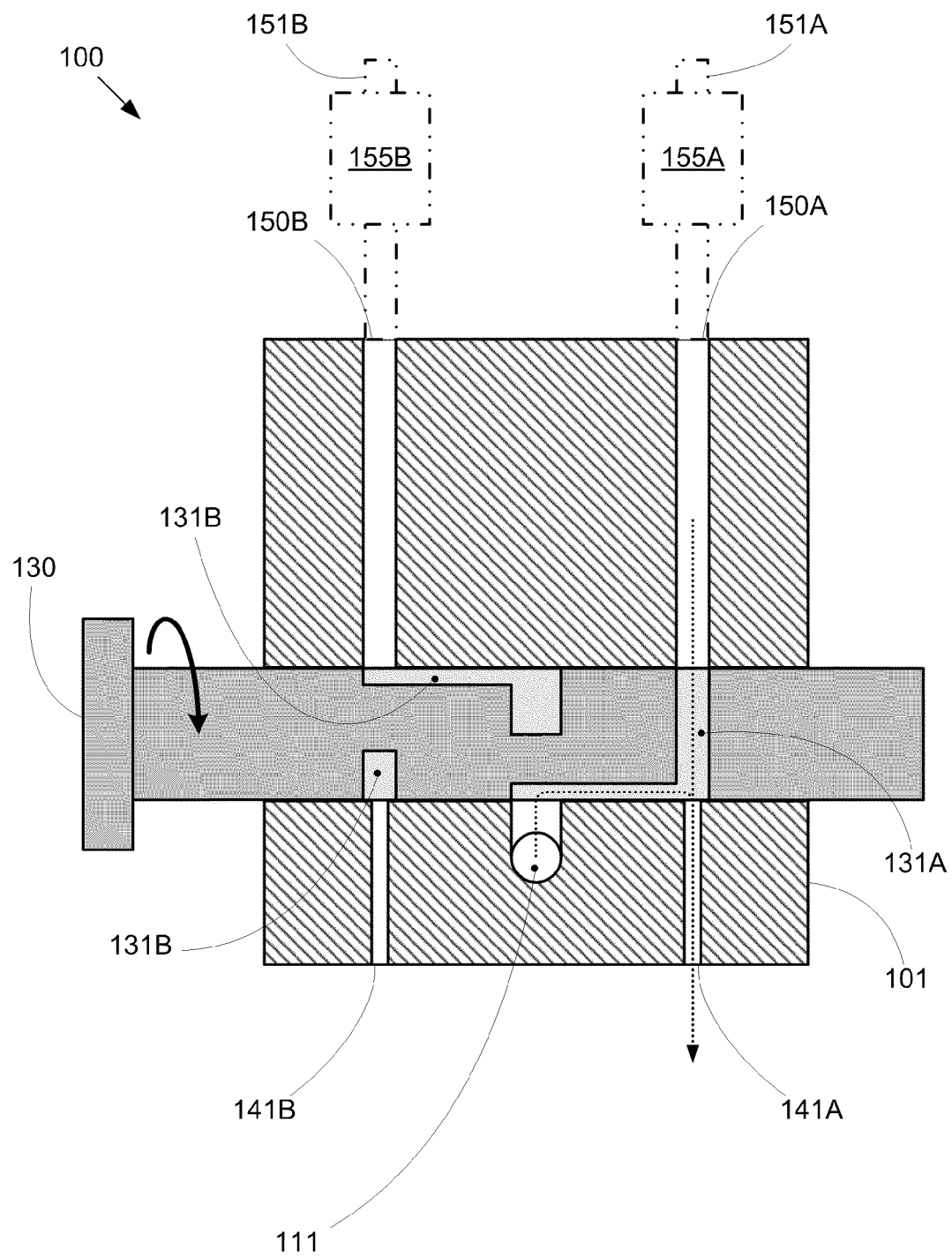

Then, as diverter 130 is rotated about its longitudinal axis as indicated in FIG. 5B, flow path 131A connects with bleed port 141A (while still connecting pressure reservoir outlet 111 to outlet 150A), thereby venting the pressure reservoir (and hence the pressure supplied to material dispensing element 155A) to the baseline pressure, as indicated by the dotted arrow.

Figure 5C:
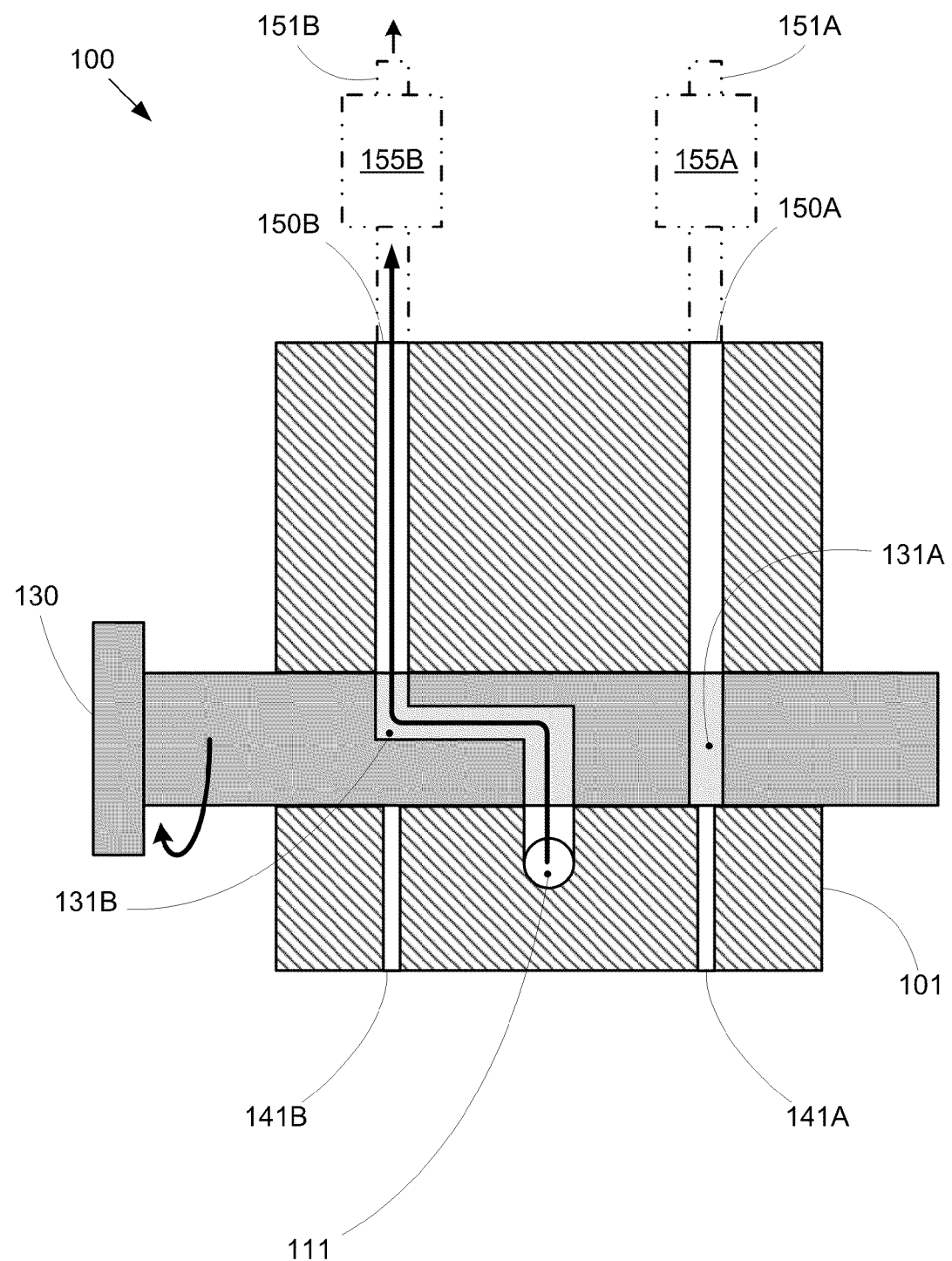

Continuing to rotate diverter 130 as indicated in FIG. 5C eventually results in flow path 131A being disconnected from pressure reservoir outlet 111 (although still connecting outlet 150A to bleed port 141A), while flow path 131B disconnects from bleed port 141B but connects pressure reservoir outlet 111 to outlet 150B. As a result, material can be dispensed from material dispensing element 155B in response to pressure generated within the pressure reservoir, while pressure outlet 150A remains at the baseline pressure to prevent unintentional discharge from material delivery element 155A.

Figure 5D:
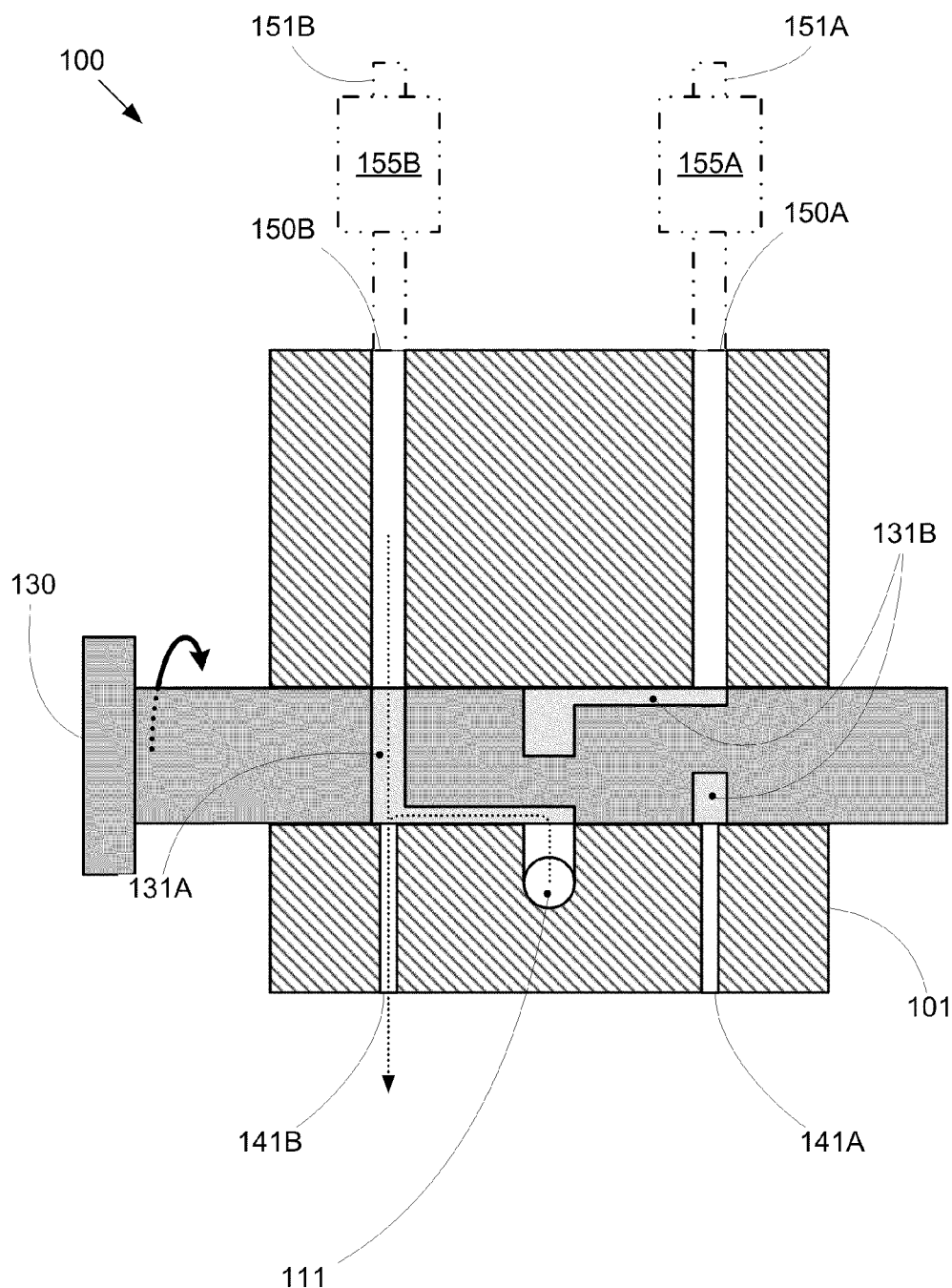

After desired material dispensing from material delivery element 155B, diverter 130 can be further rotated to cause flow path 131B to connect with bleed port 141B (while still connecting pressure reservoir outlet 111 to outlet 150B), as shown in FIG. 5D. The pressure reservoir (and outlet 150B at material delivery element 155B) are therefore vented in preparation for switching output back to material delivery element 155A. Note that while a continuous rotation mode of operation (i.e., rotating diverter 130 in a single direction to switch outputs) is described for exemplary purposes, in various other embodiments, output switching can be performed by rotating diverter 130 between particular angular orientations (i.e., rotating back and forth).

Figure 3A:
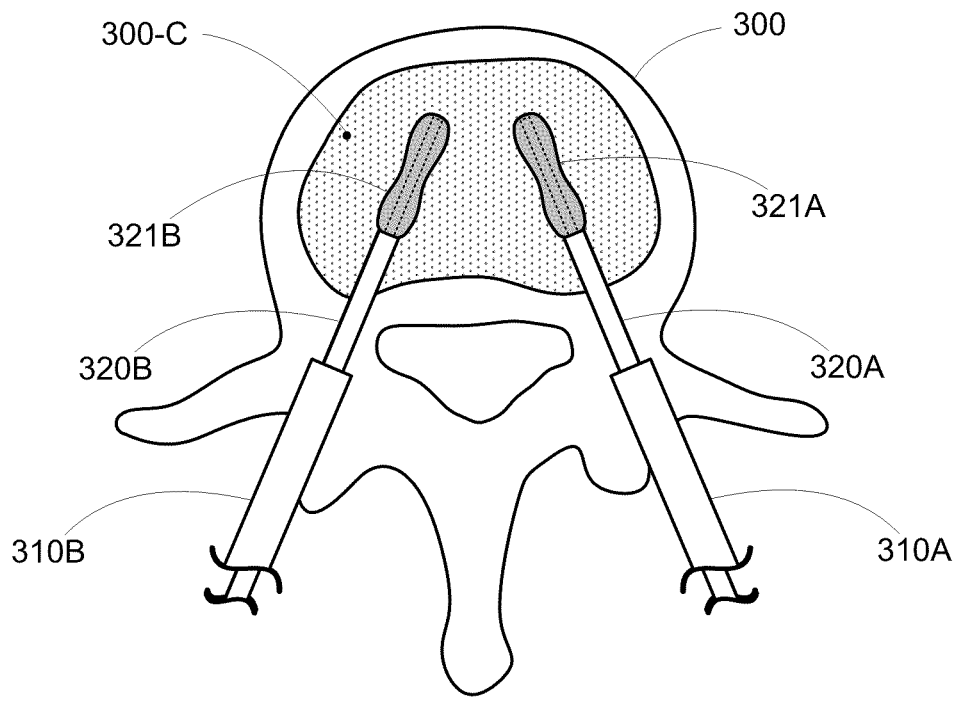
FIGS. 3A-3G show an exemplary bilateral kyphoplasty procedure performed using the multi-output material delivery system of FIGS. 2A-2F.

FIGS. 3A-3G show an exemplary use of material delivery system 100 in a kyphoplasty procedure. In FIG. 3A, cannulas 310A and 310B are positioned within a fractured vertebra 300, thereby providing an access path to the target surgical location, which in this case is the cancellous bone structure 300-C within vertebra 300. Typically, cannulas 310A and 3106 are docked into the exterior wall of vertebral body 300 (using either a transpedicular or extrapedicular approach) using a guide needle and/or dissector, after which a drill or other access tool (not shown) is used to create a path further into cancellous bone 300-C. However, any other method of cannula placement can be used.

Figure 3B:
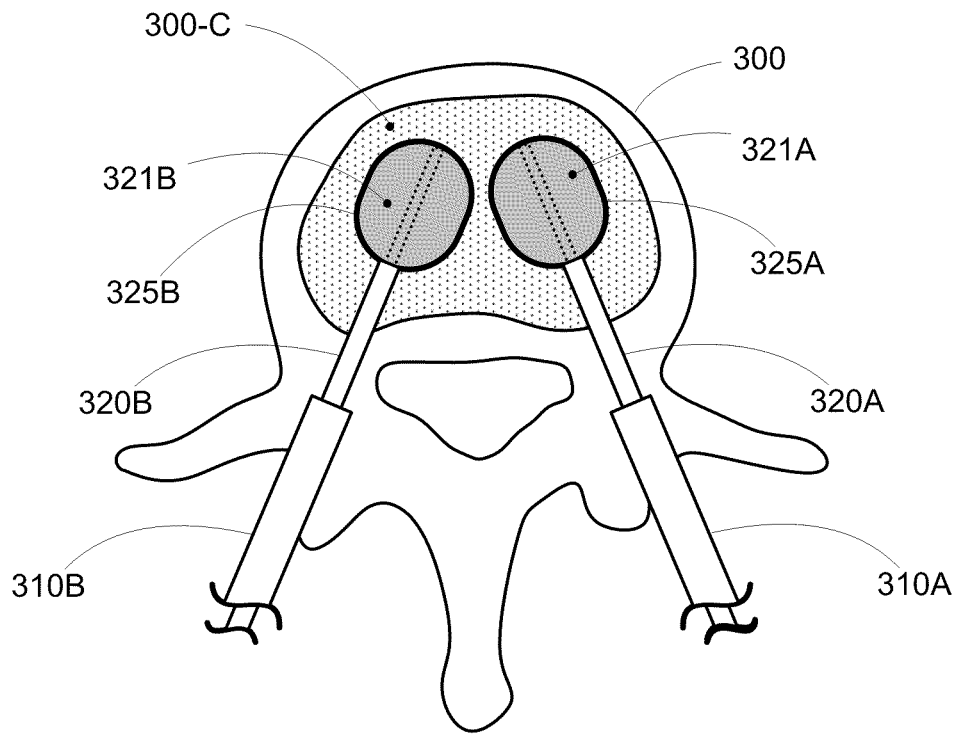

Next, cavity-creation tools such as inflatable bone tamps 320A and 320B are placed into cannulas 310A and 3106, respectively, to position expandable members (e.g., balloons) 321A and 321B, respectively, within cancellous bone 300-C. Expandable members 321A and 321B are then expanded as shown in FIG. 3B to create cavities 325A and 325B, respectively, within cancellous bone 300-C.

Figure 3C:
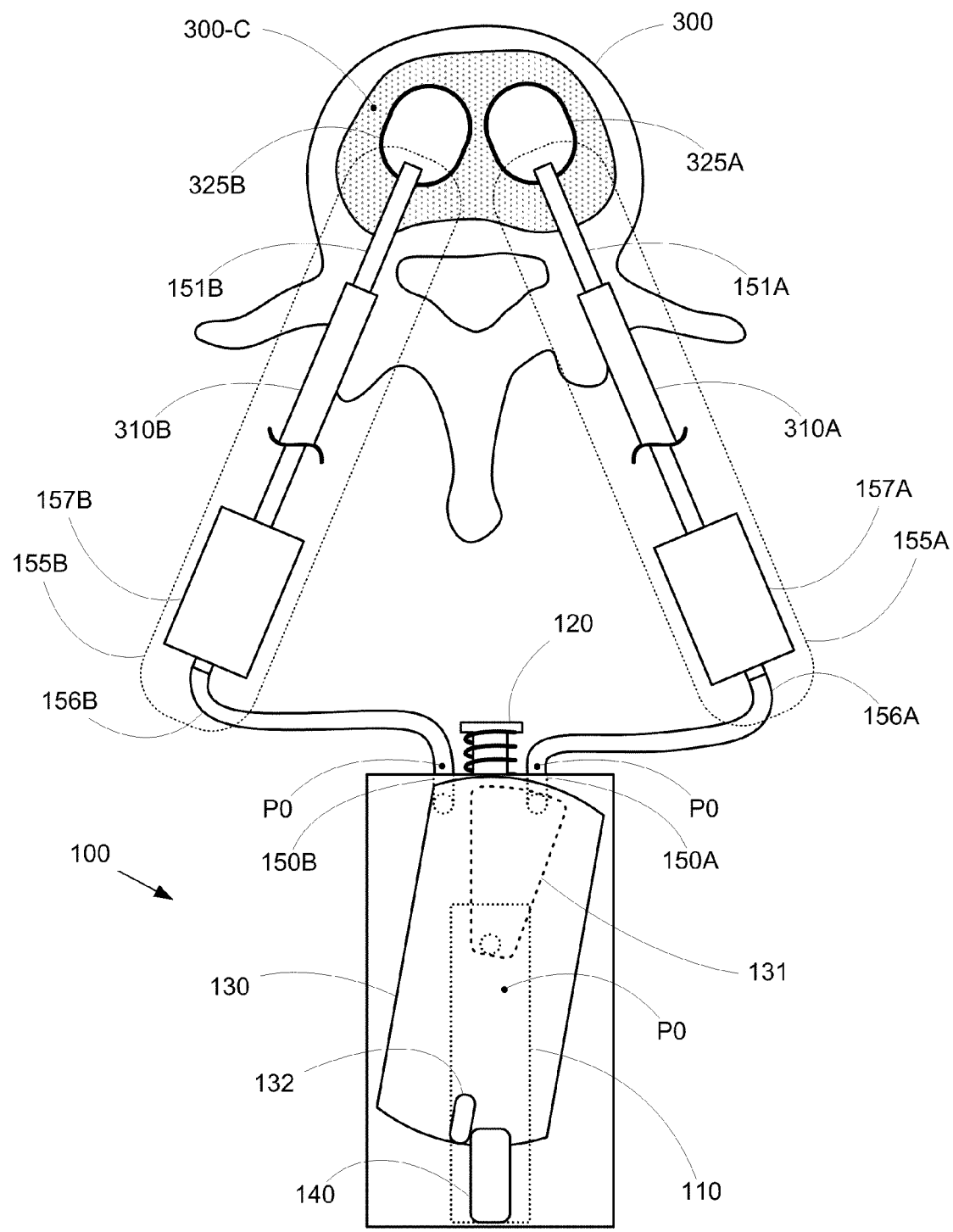

Inflatable bone tamps 320A and 320B are then removed and replaced with material delivery elements 155A and 155B, respectively, coupled to material delivery system 100 (as described with respect to FIGS. 2A-2E) as shown in FIG. 3C. For exemplary purposes, material dispensing elements 155A and 155B are coupled to pressure outlets 150A and 150B, respectively, by flexible hydraulic lines (tubing) 156A and 156B. This enables delivery control from a distance, which beneficially allows the physician to perform the material delivery procedure from outside the fluoroscopic field generated during radioscopic visualization of vertebral body 300. Note, however, that in various other embodiments, pressure outlets 150A and 150B can be coupled to material dispensing elements 155A and 155B, respectively, by more rigid structures.

For exemplary purposes, material dispensing elements 155A and 155B are depicted as including storage chambers 157A and 157B, respectively, and long, thin dispensing outlets (nozzles) 151A and 151B, respectively, that are sized to fit through cannulas 310A and 310B, respectively. Storage chambers 157A and 157B hold an amount of bone filler material that can be delivered to cavities 325A and 325B, respectively, via elongate nozzles 151A and 151B, respectively.

For exemplary purposes, diverter 130 is initially positioned to couple pressure reservoir 110 to material delivery element 155A. However, diverter 130 can be switched to the opposite position (i.e., coupling pressure reservoir 110 to material delivery element 155B) or can even be in the mid-point position (i.e., coupling pressure reservoir 110 to both material delivery elements 155A and 155B and opening release valve 140), before switching to a desired one of material delivery elements 155A and 155B.

Figure 3D:
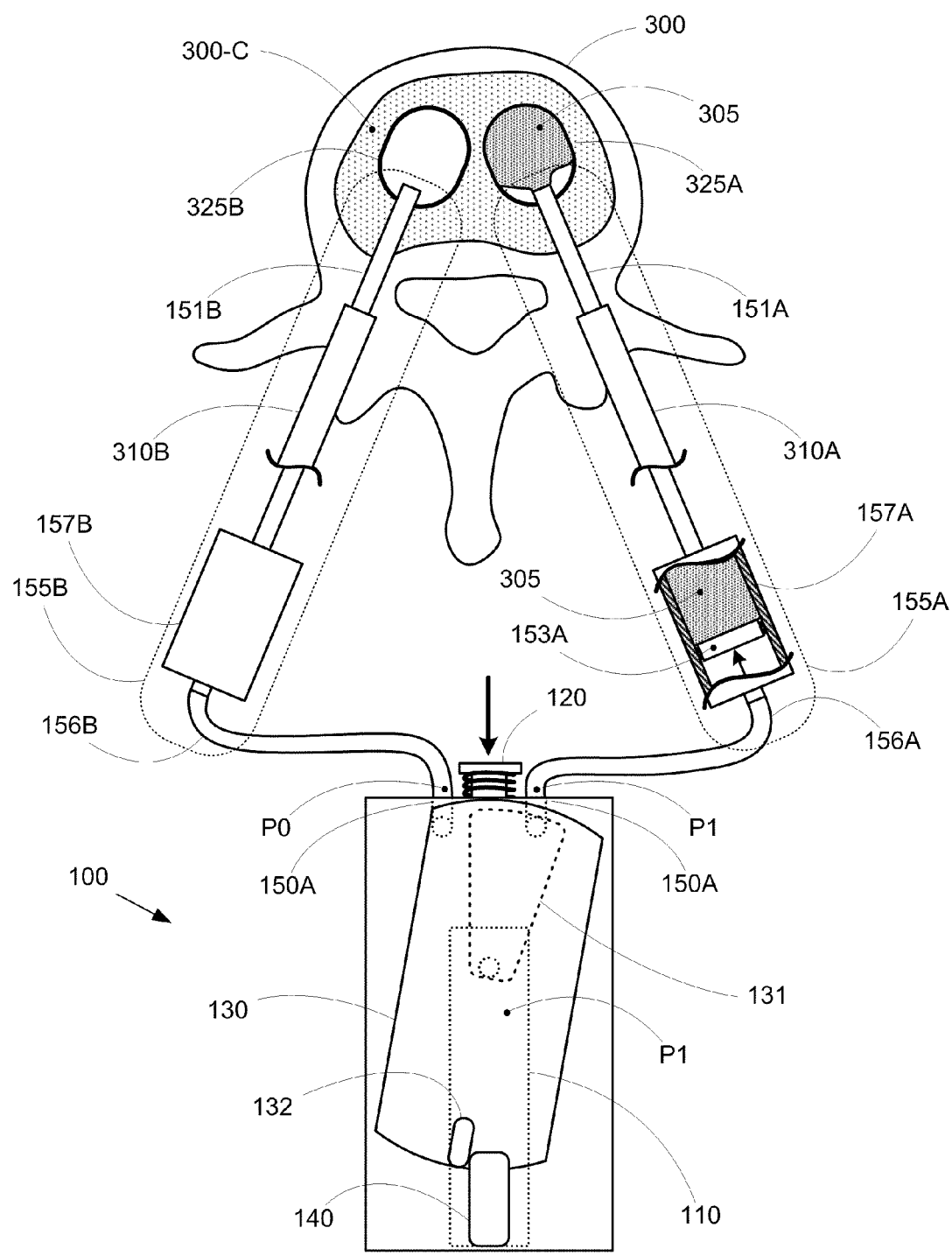

To begin filling cavity 325A, pressure source 120 is used to pressurize pressure reservoir 110, thereby forcing bone filler material 305 from material dispensing element 155A, as shown in FIG. 3D. In the embodiment shown, storage chamber 157A includes a piston 153A that expresses bone filler material 305 through delivery nozzle 151A and into cavity 325A in response to hydraulically-delivered pressure P1 from pressure reservoir 110.

Figure 3E:
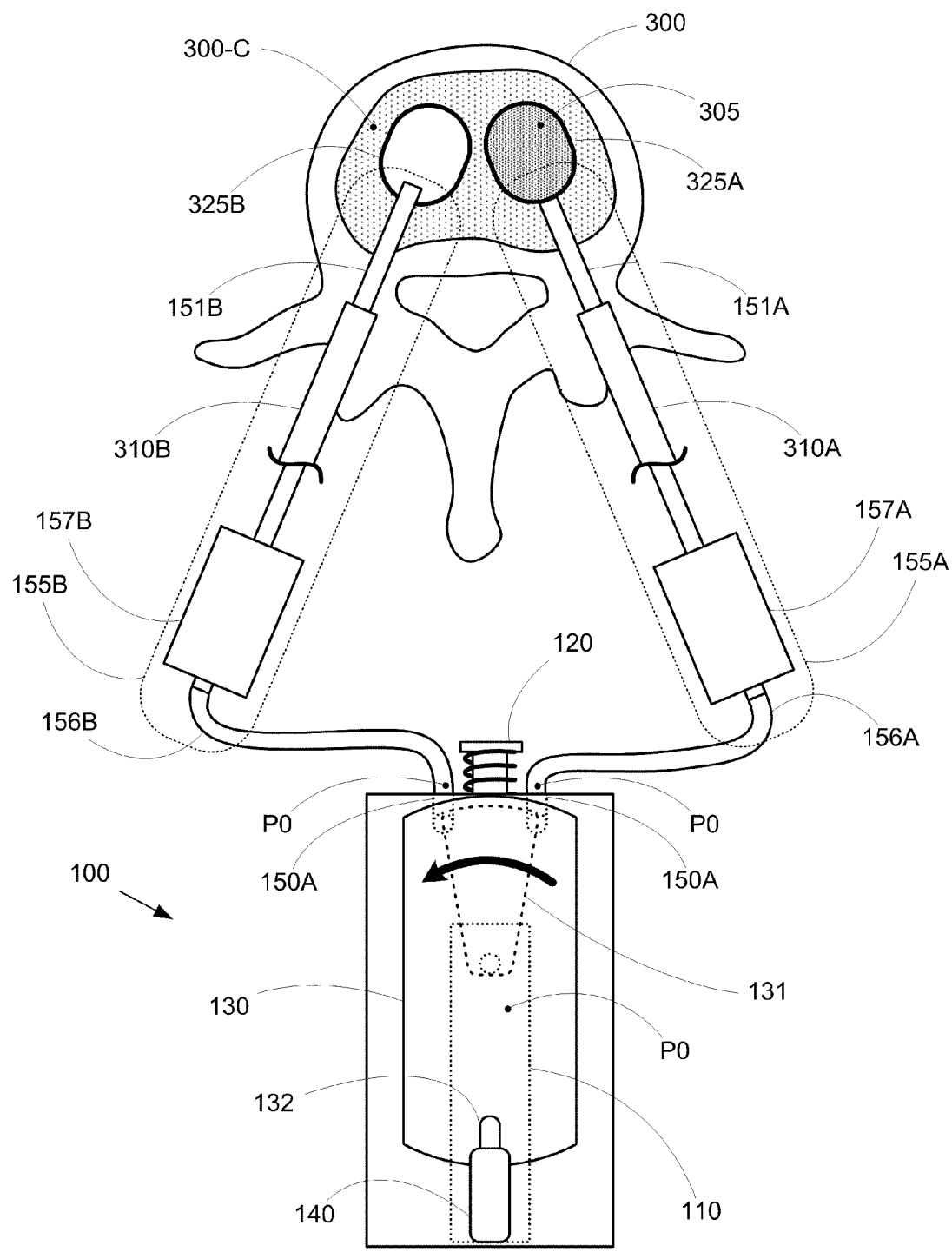

Once a sufficient amount of bone filler material 305 is delivered to cavity 325A, diverter 130 can be used to switch the output of material delivery system 100. As described with respect to FIGS. 2C and 2D, initiating this switching process as shown in FIG. 3E can open pressure release valve 140 (via triggering feature 132) to vent pressure reservoir 110 to the predetermined baseline pressure P0 (e.g., ambient pressure). In conjunction, flow path 131 of diverter couples both material dispensing elements 155A and 155B to pressure reservoir 110, thereby ensuring that the flow of bone filler material from delivery nozzle 151A is stopped and that no unintended flow of bone filler material occurs from delivery nozzle 151B.

Figure 3F:
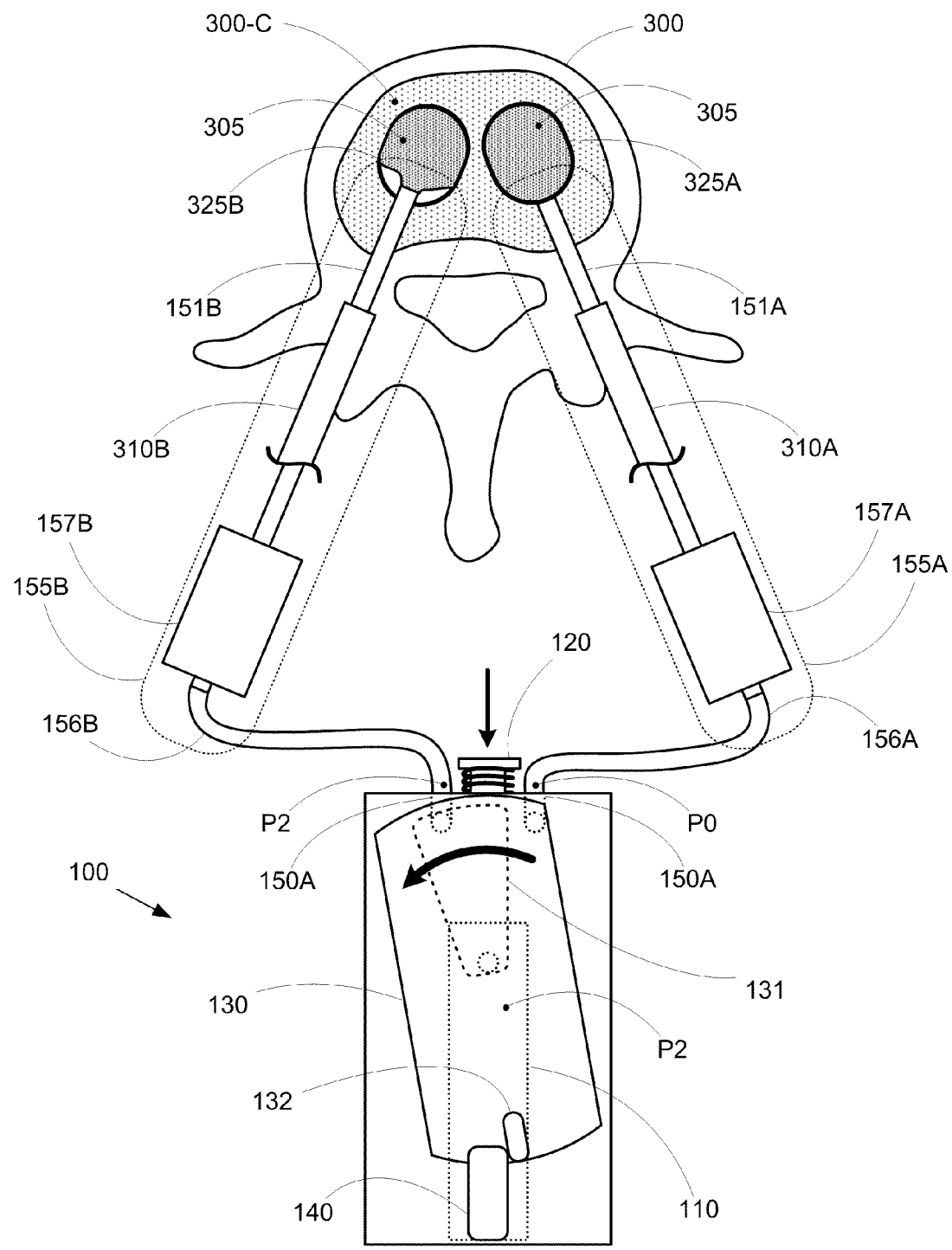

Upon completion of the switching operation of diverter 130, material dispensing element 155A is isolated from, and material dispensing element 155B is coupled to, pressure reservoir 110, as shown in FIG. 3F. Consequently, as pressure source 120 pressurizes pressure reservoir 110 anew, this new pressure P2 only drives bone filler material 305 from delivery nozzle 325B of material dispensing element 355B. In this manner, bone filler material 305 can be delivered to vertebral body 300 in a controlled and user-friendly manner.

Note that a sequential two-step bone filler material delivery operation (i.e., fill cavity 325A, and then fill cavity 325B) is described for exemplary purposes only. In various other embodiments, cavities 325A and 325B can be filled in any order, using any number of discrete filling operations. For example, cavity 325A could be partially filled via material dispensing element 155A, diverter 130 could be used to switch the output of material delivery system 100 to material dispensing element 155B to allow partial filling of cavity 325B. Diverter 130 could then switch the output back to material dispensing element 155A, to enable additional material delivery to cavity 325A. The filling process could continue alternating between cavities 325A and 325B until a desired amount of bone filler material 305 is delivered to each.

Figure 3G:
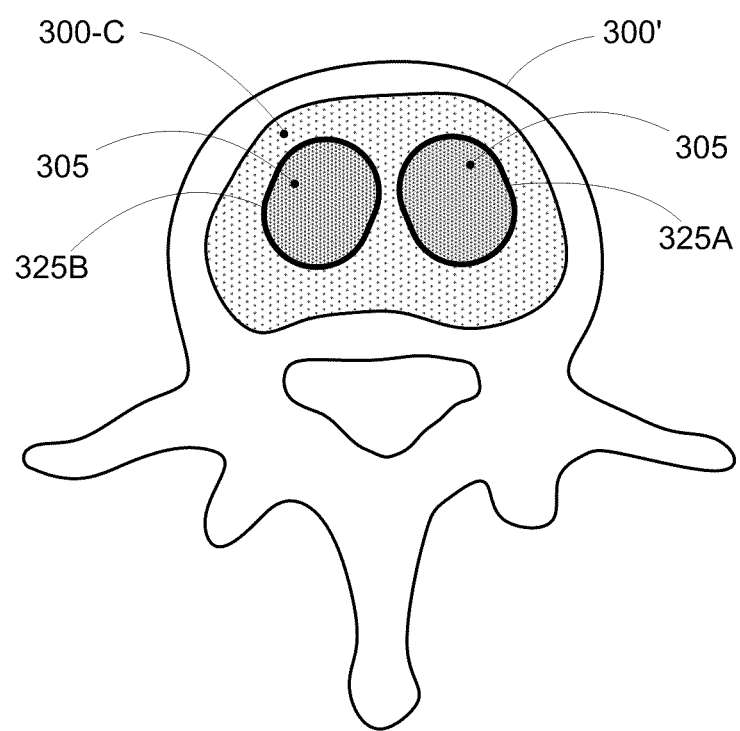

Once the filling operation is complete, delivery nozzles 151A and 151B, and cannulas 310A and 310B are removed from vertebra 300 (and the patient's body) as shown in FIG. 3G. Upon hardening, bone filler material 305 provides structural support for vertebra 300, thereby substantially restoring the structural integrity of the bone and the proper musculoskeletal alignment of the spine. In this manner, the pain and attendant side effects of a vertebral compression fracture can be addressed by the kyphoplasty procedure.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A device for performing a surgical procedure, the device comprising:
   a plurality of outputs;
   a pressure reservoir configured for selective coupling to one of the plurality of outputs;
   a pressure source for pressurizing the pressure reservoir;
   a diverter for coupling the pressure reservoir to one of the plurality of outputs, the diverter is configured for rotational movement between the one of a plurality of outputs;
   a triggering feature disposed on the diverter and including a raised element configured for opening the pressure release valve when the diverter switches between the plurality of outputs,
   a pressure release valve for venting the pressure reservoir to a baseline pressure; and
   wherein when the diverter is configured to switch between a first one of the plurality of outputs to a second one of the plurality of outputs, the triggering feature is configured to open the pressure release valve and cause the diverter to decouple the pressure reservoir from the first one of the plurality of outputs, and the triggering feature closes the pressure release valve after coupling the pressure reservoir with the second one of the plurality of outputs.

2. The device of claim 1, wherein the diverter switches between the plurality of outputs by changing orientation, wherein the triggering feature comprises a physical feature on the diverter, and wherein the physical feature contacts an actuation element of the pressure release valve when the diverter changes orientation.

3. The device of claim 1, wherein the triggering feature opens the pressure release valve while the diverter is coupled to one of the plurality of outputs to the pressure reservoir.

4. The device of claim 1, wherein the pressure reservoir contains a hydraulic fluid.

5. The device of claim 4, wherein each of the plurality of outputs comprises: a storage chamber for housing a flowable material; a piston for expressing the flowable material from the storage chamber; and a flexible hydraulic line for delivering the hydraulic fluid to the piston.

6. The device of claim 1, wherein the diverter comprises a substantially cylindrical element, and wherein selectably coupling the pressure reservoir to one of the plurality of outputs comprises rotating the diverter about a longitudinal axis of the diverter.

7. The device of claim 6, further comprising: a first bleed port, and a second bleed port, wherein the diverter defines a first flow path and a second flow path, wherein when the diverter is in a first orientation, the first flow path connects a first one of the plurality of outputs to the pressure reservoir and the second flow path connects a second one of the plurality of outputs to the second bleed port, wherein when the diverter is in a second orientation, the first flow path connects the first one of the plurality of outputs and the pressure reservoir to the first bleed port, wherein when the diverter is in a third orientation, the first flow path connects the first one of the plurality of outputs to the first bleed port and the second flow path connects the second one of the plurality of outputs to the pressure reservoir, and wherein when the diverter is in a fourth orientation, the second flow path connects the second one of the plurality of outputs and the pressure reservoir to the second bleed port.

8. The device of claim 1, wherein the pressure reservoir contains a flowable material, and wherein each of the plurality of outputs comprises: a nozzle sized to fit through a cannula; and a flexible length of tubing for delivering the flowable material from the pressure reservoir to a target surgical location.

9. The device of claim 1, wherein the pressure source comprises: a one-way check valve coupled to the pressure reservoir; a piston; a trigger for manually driving the piston to pressurize the pressure reservoir through the one-way check valve.

10. A surgical method comprising: providing the device for performing a surgical procedure of claim 1; pressurizing the a pressure reservoir of the device to express a first quantity of bone filler material from a first nozzle into a first target surgical location; decoupling the first nozzle from the pressure reservoir; coupling a second nozzle to the pressure reservoir; and pressurizing the pressure reservoir to express a second quantity of bone filler material from the second nozzle into a second target surgical location.

11. The surgical method of claim 10, wherein decoupling the first nozzle from the pressure reservoir comprises venting the pressure reservoir to a baseline pressure while the first nozzle remains coupled to the pressure reservoir and then decoupling the first nozzle from the pressure reservoir.

12. The surgical method of claim 11, wherein venting the pressure reservoir to the baseline pressure comprises opening a pressure release valve coupled to the pressure reservoir, and wherein coupling the second nozzle to the pressure reservoir comprises coupling the second nozzle to the pressure reservoir while maintaining the release valve in an open condition, and then closing the pressure release valve.

13. The surgical method of claim 12, wherein venting the pressure reservoir while the first nozzle remains coupled to the pressure reservoir occurs concurrently with coupling the second nozzle to the pressure reservoir while maintaining the pressure release valve in an open condition.

14. The surgical method of claim 13, wherein pressurizing the pressure reservoir to express the first quantity of bone filler material from the first nozzle into the first target surgical location comprises: providing a hydraulic fluid in the pressure reservoir; providing a first length of flexible tubing between a first pressure outlet and a first storage chamber; and positioning a flow path between the pressure reservoir and the first pressure outlet, wherein the first quantity of bone filler material is expressed from the first storage chamber through the first nozzle in response to the hydraulic fluid flow through the first length of flexible tubing.

15. The surgical method of claim 14, wherein pressurizing the pressure reservoir to express the second quantity of bone filler material from the second nozzle into the second target surgical location comprises: providing a second length of flexible tubing between a second pressure outlet and a second storage chamber; and positioning the flow path between the pressure reservoir and the second pressure outlet, wherein the second quantity of bone filler material is expressed from the second storage chamber through the second nozzle in response to the hydraulic fluid flow through the second length of flexible tubing.

16. The surgical method of claim 15, wherein venting the pressure reservoir while the first nozzle remains coupled to the pressure reservoir comprises positioning the flow path between the pressure reservoir and the first and second pressure outlets.

17. The surgical method of claim 10, further comprising: decoupling the second nozzle from the pressure reservoir; re-coupling the first nozzle to the pressure reservoir; and pressurizing the pressure reservoir to express a third quantity of bone filler material from the first nozzle into the first target surgical location.

18. The surgical method of claim 10, further comprising: decoupling the second nozzle from the pressure reservoir; coupling a third nozzle to the pressure reservoir; and pressurizing the pressure reservoir to express a third quantity of bone filler material from the third nozzle into a third target surgical location.

19. A device for performing a surgical procedure, the device comprising:
a plurality of outputs;
a pressure reservoir;
a pressure source for pressurizing the pressure reservoir;
a diverter configured to define a flow path between the pressure reservoir and the plurality of outputs such that the diverter simultaneously couples the pressure reservoir the plurality of outputs such that material can be dispensed into a surgical site from at least two of the plurality of outputs simultaneously, the diverter is configured for rotational movement between the one of a plurality of outputs; and
a triggering feature disposed on the diverter and including a raised element configured for opening a pressure release valve when the diverter switches between the plurality of outputs.

20. A device for performing a surgical procedure, the device comprising:
a plurality of outputs;
a pressure reservoir configured for selective coupling to one of the plurality of outputs;
a pressure source for pressurizing the pressure reservoir;
a diverter for selectably coupling the pressure reservoir to one of the plurality of outputs;
a pressure release valve for venting the pressure reservoir to a baseline pressure, wherein the diverter comprises a triggering feature for opening the pressure release valve when the diverter switches between any of the plurality of outputs and
a first bleed port, and a second bleed port, wherein the diverter defines a first flow path and a second flow path,
wherein when the diverter is in a first orientation, the first flow path connects a first one of the plurality of outputs to the pressure reservoir and the second flow path connects a second one of the plurality of outputs to the second bleed port,
wherein when the diverter is in a second orientation, the first flow path connects the first one of the plurality of outputs and the pressure reservoir to the first bleed port,
wherein when the diverter is in a third orientation, the first flow path connects the first one of the plurality of outputs to the first bleed port and the second flow path connects the second one of the plurality of outputs to the pressure reservoir, wherein when the diverter is in a fourth orientation, the second flow path connects the second one of the plurality of outputs and the pressure reservoir to the second bleed port, and wherein when the diverter is configured to switch between a first one of the plurality of outputs to a second one of the plurality of outputs, the triggering feature configured to open the pressure release valve and cause the diverter to decouple the pressure reservoir from the first one of the plurality of outputs, and the triggering feature closes the pressure release valve after coupling the pressure reservoir with the second one of the plurality of outputs.

\* \* \* \* \*

UNITED STATES PATENT AND TRADEMARK OFFICE
CERTIFICATE OF CORRECTION

PATENT NO.        : 8,876,833 B2                                       Page 1 of 1
APPLICATION NO.   : 12/771812
DATED             : November 4, 2014
INVENTOR(S)       : Donovan et al.

It is certified that error appears in the above-identified patent and that said Letters Patent is hereby corrected as shown below:

In The Drawings

In Fig. 3G, Sheet 11 of 18, delete Tag "300'" and insert -- 300 --, therefor.

In The Specification

In Column 3, Line 54, delete "1506," and insert -- 150B, --, therefor.

In Column 4, Lines 5-6, delete "morphongenic" and insert -- morphogenic --, therefor.

In Column 6, Line 48, delete "reservoir 100" and insert -- reservoir 110 --, therefor.

In Column 8, Line 34, delete "3106" and insert -- 310B --, therefor.

In Column 8, Line 41, delete "3106," and insert -- 310B, --, therefor.

In Column 9, Line 1, delete "3256," and insert -- 325B, --, therefor.

In Column 9, Line 29, delete "1558" and insert -- 155B --, therefor.

In Column 9, Line 35, delete "1556" and insert -- 155B --, therefor.

Signed and Sealed this
Twenty-eighth Day of April, 2015

Michelle K. Lee
*Director of the United States Patent and Trademark Office*